US012644798B2

(12) United States Patent
Westlund

(10) Patent No.: US 12,644,798 B2
(45) Date of Patent: Jun. 2, 2026

(54) SYSTEM AND METHOD FOR FLUID SAMPLING

(71) Applicant: C.E.C. INNOVATIONS LTD., Calgary (CA)

(72) Inventor: Paul Alexander Westlund, Calgary (CA)

(73) Assignee: C.E.C. INNOVATIONS LTD., Calgary (CA)

( * ) Notice: Subject to any disclaimer, the term of this patent is extended or adjusted under 35 U.S.C. 154(b) by 519 days.

(21) Appl. No.: 18/253,336

(22) PCT Filed: Nov. 18, 2021

(86) PCT No.: PCT/CA2021/051634
§ 371 (c)(1),
(2) Date: May 17, 2023

(87) PCT Pub. No.: WO2022/104466
PCT Pub. Date: May 27, 2022

(65) Prior Publication Data
US 2024/0077388 A1      Mar. 7, 2024

Related U.S. Application Data

(60) Provisional application No. 63/115,244, filed on Nov. 18, 2020.

(51) Int. Cl.
*G01N 1/14*          (2006.01)
*G01N 1/10*          (2006.01)
(Continued)

(52) U.S. Cl.
CPC ............. *G01N 1/14* (2013.01); *G01N 1/4077* (2013.01); *G01N 33/18* (2013.01);
(Continued)

(58) Field of Classification Search
CPC ................... G01N 1/14; G01N 1/4077; G01N 2001/1006; G01N 2001/4083;
(Continued)

(56) References Cited

U.S. PATENT DOCUMENTS

| 6,478,961 | B2 | 11/2002 | Petty et al. |
| 7,199,145 | B2 | 4/2007 | Poitout et al. |
| 2020/0072709 | A1* | 3/2020 | Matus Garcia .......... G01N 1/20 |

FOREIGN PATENT DOCUMENTS

| GB | 720161 A | 12/1954 |
| WO | 2020160599 A1 | 8/2020 |

OTHER PUBLICATIONS

International Search Report and Written Opinion mailed Feb. 14, 2022 in International Patent Application No. PCT/CA2021/051634 (8 pages).

(Continued)

*Primary Examiner* — Jennifer Wecker
*Assistant Examiner* — Jonathan Bortoli
(74) *Attorney, Agent, or Firm* — SMART & BIGGAR LP; Tonino Rosario Orsi

(57) ABSTRACT

A container comprising a fluid sampling system configured for the flow of particulate containing fluid therethrough are provided. The particulate containing fluid enters the container from the exterior through a fluid inlet and flows through a fluid flow path which includes at least two serially fluidically coupled sample collection vessels, which are releasably installed in the container. Fluid flow through the fluid flow path is controlled by a fluid pump in a manner that allows for sequential receipt of the particulate containing fluid in the sample collection vessels, and for particulates in the particulate containing fluid to settle in at least one of the sample collection vessels. Upon receipt and settlement of the particulates, the container can be opened and the sample (Continued)

collection vessels can be released from the container Related methods for operating the fluid sampling systems are also provided.

20 Claims, 12 Drawing Sheets

(51) Int. Cl.
        *G01N 1/40*          (2006.01)
        *G01N 33/18*        (2006.01)

(52) U.S. Cl.
        CPC ................ *G01N 2001/1006* (2013.01); *G01N 2001/4083* (2013.01); *G01N 2001/4088* (2013.01)

(58) Field of Classification Search
        CPC . G01N 2001/4088; G01N 2035/00445; G01N 33/18
        See application file for complete search history.

(56)                  References Cited

OTHER PUBLICATIONS

Corpuz et al., "Viruses in wastewater: occurrence, abundance and detection methods" (2020) Science of the Total Environment, 745, 140910.
Rao et al., "Isolation of enteroviruses from water, suspended solids, and sediments from Galveston Bay: survival of poliovirus and rotavirus adsorbed to sediments." (1984) Appl Environ Microbiol 48:404-409.

* cited by examiner

200

122

122

122d1

122c

122e

106a

106b

106c

106d

122d3

122d2

705 — Install Sampling System with Inlet Coupled to Source Fluid

700

710 — Activate Pump

715 — Deactivate Pump

720 — Retrieve Sampling System

705 — Install Sampling System with Inlet Coupled to Source Fluid

710 — Activate Pump

715 — Deactivate Pump

720 — Retrieve Sampling System

725 — Release Fluid Collection Vessels

701

705 — Install Sampling System with Inlet Coupled to Source Fluid

710 — Activate Pump

715 — Deactivate Pump

720 — Retrieve Sampling System

725 — Release Fluid Collection Vessels

730 — Collect Fluid and/or Particulate Fraction

702

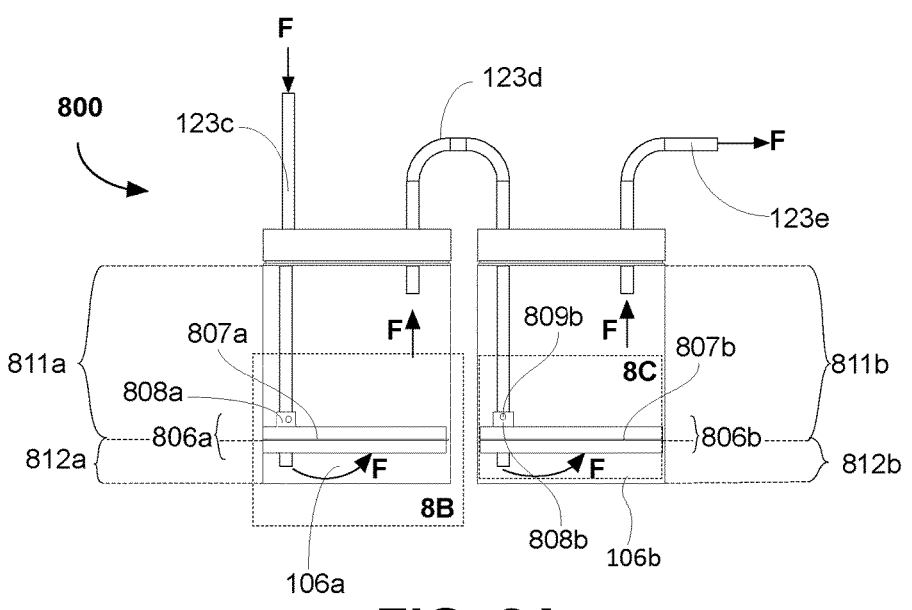
FIG. 8A
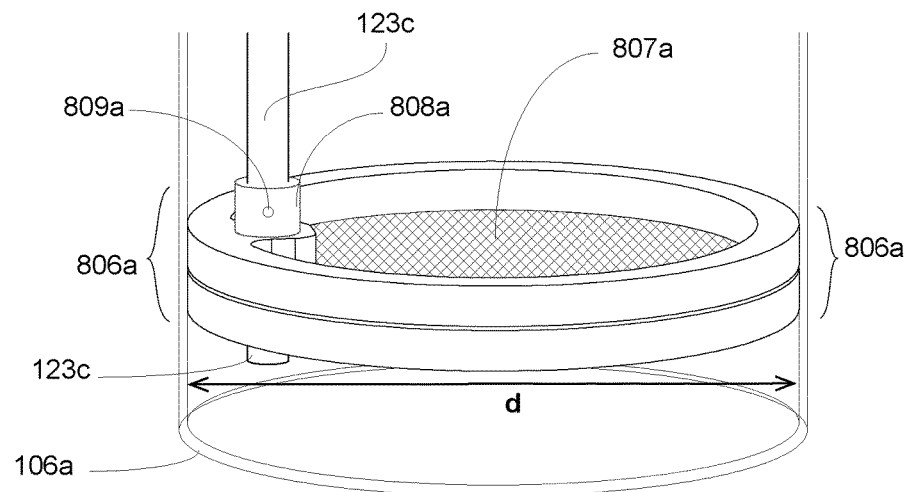
FIG. 8B
FIG. 8C

SYSTEM AND METHOD FOR FLUID SAMPLING

CROSS-REFERENCE TO RELATED APPLICATIONS

This application is a national phase entry of PCT/CA2021/051634 filed Nov. 18, 2021 (which designates the U.S.), which claims priority from U.S. Provisional Patent Application No. 63/115,244, filed on Nov. 28, 2020, the entire contents of which is hereby incorporated herein by reference in its entirety.

FIELD OF THE DISCLOSURE

The present disclosure generally relates to systems and methods for fluid sampling, and in particular to systems and methods for the collection of particulate containing fluid samples.

BACKGROUND

The following paragraphs are provided by way of background to the present disclosure. They are not however an admission that anything discussed therein is prior art or part of the knowledge of persons skilled in the art.

There are many circumstances in which fluid testing is desirable. For example, water can contain chemical or biological substances, such as a water borne pathogens, which must be monitored and maintained within certain tolerances in order to ensure a safe supply of drinking water for domestic purposes. Similarly, wastewater, including domestic and industrial wastewater, must meet certain quality standards in order to be safely discharged. Consequently, a variety of systems and techniques to collect water and other fluid samples and monitor chemical and biological entities therein have been developed.

However, one substantial ongoing challenge associated with the detection and quantification of chemical or biological attributes in fluid samples arises from the complexity of the fluid samples. In this respect, wastewater samples, also commonly referred to as "effluent samples", can be said to be particularly heterogeneous. In particular, the presence of particulate matter in the form of suspended solids in wastewater samples can be problematic and can compromise the detection of chemical or biological entities in wastewater samples. For example, suspended solids are known to absorb viral particles, and thus interfere with detection or quantification thereof in wastewater samples (see e.g, Corpuz, M. V. A. et al., 2020, Science of the Total Environment, 745, 140910; Chalapati, R. et al., 1984, Appl. and Environ. Microbiol. 404-409).

The ongoing challenges with known systems to collect fluid samples necessitate improved systems and techniques to collect fluid samples, and notably there is a need in the art for systems and techniques to collect fluid samples comprising particulate matter.

SUMMARY

The following paragraphs are intended to introduce the reader to the more detailed description that follows and not to define or limit the claimed subject matter of the present disclosure.

In one broad aspect, the present disclosure relates to systems for the collection of fluid samples.

Accordingly, in one aspect, in accordance with the teachings herein, the present disclosure provides, in at least one aspect, in at least one embodiment, an openable container constructed and arranged for the flow of particulate containing fluids therethrough, the container comprising:

a sampling system for the collection of fluids, the sampling system comprising:

a fluid inlet in fluid communication with an exterior of the container to receive particulate containing fluids;

at least two serially fluidically coupled sample collection vessels releasably installed in the container and coupled to the fluid inlet, the sample collection vessels including a first sample collection vessel nearest the fluid inlet and a final sample collection vessel;

a fluid flow path through the container from the fluid inlet serially through the at least two sample collection vessels;

a fluid pump that is operably coupled to the fluid flow path and is configured to control the flow of the particulate containing fluids through the fluid flow path; and a controller configured to control the flow of the particulate containing fluids through the fluid flow path;

wherein during use when the container is in a closed position and the fluid inlet being in fluid communication with a source of particulate containing fluid exterior to the container, the controller is configured to activate the fluid pump at a first time to cause a portion of the particulate containing fluid to enter the container through the fluid inlet and to flow through the fluid flow path at a rate such that the particulate containing fluid is sequentially received by the serially fluidically coupled sample collection vessels, and particulates in the particulate containing fluid settle in the sample collection vessels, the controller further being configured to deactivate the fluid pump at a second time to stop collection of the particulate containing fluid.

In at least one embodiment, in an aspect, the final sample collection vessel can be fluidically coupled to a fluid outlet in fluid communication with the exterior, the fluid flow path extending from the final sample collection vessel to the fluid outlet.

In at least one embodiment, in an aspect, the fluid pump can be controlled to pump the fluid through the fluid flow path at a selected rate wherein a greater quantity of the particulates settles in the first sample collection vessel compared to the final sample collection vessel.

In at least one embodiment, in an aspect, the sampling system can comprise two serially coupled sample collection vessels.

In at least one embodiment, in an aspect, the sample collection system can comprise three or more serially coupled sample collection vessels.

In at least one embodiment, in an aspect, the fluid flow path can comprise a fluid coupling system for at least one of the sample collection vessels, the fluid coupling system comprising a sample collection vessel fluid inlet and a sample collection vessel fluid outlet disposed in the at least one sample collection vessel, the sample collection vessel fluid inlet comprising a tubular fluid inlet conduit traversing a top portion of the at least one sample collection vessel at a first aperture and extending downwards therefrom to approximately a bottom portion of the at least one sample collection vessel to permit receipt of incoming fluid at approximately the bottom of the sample collection vessel, and the sample collection vessel fluid outlet comprises a tubular fluid outlet conduit traversing the top portion of the sample collection vessel at a second aperture and extending downwards therefrom no further than to approximately half a height of the at least one sample collection vessel to permit transfer of outgoing fluid downstream from the at least one sample collection vessel.

In at least one embodiment, in an aspect, the fluid flow path can further include a filter to collect selected chemical or biological species from the particulate containing fluid.

In at least one embodiment, in an aspect, the filter can be installed in the fluid flow path between the fluid inlet and the first sample collection vessel.

In at least one embodiment, in an aspect, the filter can be installed in the fluid flow path between the first sample collection vessel and the final sample collection vessel of the at least two serially coupled sample collection vessels.

In at least one embodiment, in an aspect, the filter can be installed in the fluid flow path in at least one of the sample collection vessels, the filter being disposed within the at least one sample collection vessel at a height above the height of a terminal end of the tubular fluid inlet conduit of the at least one sample collection vessel fluid inlet and so that incoming fluid is received by the at least one sample collection vessel, then traverses the filter, and the outgoing fluid then transfers downstream from the at least one sample collection vessel.

In at least one embodiment, in an aspect, the filter can be detachably coupled to the tubular fluid inlet conduit of the at least one sample collection vessel fluid inlet.

In at least one embodiment, in an aspect, filters can be installed in the fluid flow path in all of the sample collection vessels.

In at least one embodiment, in an aspect, the fluid inlet can include a terminal end that extends to the exterior of the container, and the terminal end includes a mesh filter configured to prevent the entry of debris into the container.

In at least one embodiment, in an aspect, the container can be compartmentalized and includes a coolable compartment that is configured to house the sample collection vessels.

In at least one embodiment, in an aspect, the coolable compartment can be configured to hold ice packs.

In at least one embodiment, in an aspect, the container can include a cooling device controlled by a controller to control the temperature of the coolable compartment.

In at least one embodiment, in an aspect, the temperature in the coolable compartment can be controlled to be in a range from about 2° C. to about 10° C.

In at least one embodiment, in an aspect, the controller can be coupled to an environmental sensor capable of detecting a change in an environmental parameter, and the controller can be configured to activate the fluid pump upon the detection of a change in an environmental parameter by the sensor.

In at least one embodiment, in an aspect, the environmental sensor can be a rain sensor, a pH sensor, a temperature sensor, a turbidity sensor, a biochemical oxygen demand (BOD) sensor, a chemical oxygen demand (COD), an electrical conductivity (EC) sensor, or a total dissolved solids (TDS) sensor.

In at least one embodiment, in an aspect, the particulate containing fluid source can be wastewater.

In at least one embodiment, in an aspect, the openable container can comprise an openable lid and when the lid of the container is in a closed position the sampling system is operable.

In at least one embodiment, in an aspect, the openable container can comprise a linking portion to attach the container to a suspension arrangement.

In another aspect, in accordance with the teachings herein, the present disclosure provides, in at least one aspect, in at least one embodiment, a method of collecting samples using the openable container comprising the fluid sampling system according to the present disclosure, the method comprising:

installing the container in a closed position in such a manner that the fluid inlet is fluidically coupled to a source of particulate containing fluid;

activating the fluid pump at a first time to cause a portion of the particulate containing fluid to enter the container through the fluid inlet and flow through the container through the fluid flow path at a rate that allows particulates in the particulate containing fluid to settle in at least one of the sample collection vessels to separate from the fluid, deactivating the fluid pump at a second time to thereafter permit release of the sample collection vessels from the container; and retrieving the container.

In at least one embodiment, in an aspect, the method can further comprise opening the container and releasing the sample collection vessels.

In at least one embodiment, in an aspect, the method can further comprise collecting a settled particulate fraction and/or a liquid fraction from the released sample collection vessels.

In at least one embodiment, in an aspect, the method can further comprise assaying a chemical or biological parameter in the settled particulate fraction and/or the liquid fraction.

In at least one embodiment, in an aspect, a terminal end of the fluid inlet can be suspended in a stagnant fluid source.

In at least one embodiment, in an aspect, a terminal end of the fluid inlet can be suspended in a flowing fluid source.

In at least one embodiment, in an aspect, a terminal end of the fluid inlet can be suspended in the wastewater fluid source.

In at least one embodiment, in an aspect, the method comprises periodically activating and deactivating the fluid pump.

In at least one embodiment, in an aspect, each period of activating and deactivating the pump is separated by a hold time interval during which no fluid flows through the fluid path.

In at least one embodiment, in an aspect, the periodic activating and deactivating is continued until the sample collection vessels are full.

In at least one embodiment, in an aspect, the method comprises periodically activating the fluid pump at a first time and deactivating the fluid pump at a second time, wherein each period is separated by a hold time interval during which no fluid flows through the fluid path, wherein the second time occurs from about 5 seconds to about 30 seconds later than the first time, and wherein the hold time interval is at least 15 minutes.

In at least one embodiment, in an aspect, the method can comprise activating the fluid pump upon an environmental sensor detecting a change in an environmental parameter.

In at least one embodiment, in an aspect, the method comprises activating the fluid pump upon an environmental sensor detecting a change in an environmental parameter, and deactivating the fluid pump at a set time thereafter, or deactivating the fluid pump when the sample collection vessels are full.

In at least one embodiment, in an aspect, the environmental sensor is a rain sensor, a pH sensor, a temperature sensor, a turbidity sensor, a biochemical oxygen demand (BOD) sensor, a chemical oxygen demand (COD), an electrical conductivity (EC) sensor, or a total dissolved solids (TDS) sensor.

In another aspect, in accordance with the teachings herein, the present disclosure provides, in at least one aspect, in at least one embodiment, a use of the openable container comprising a fluid sampling system according to the present disclosure, to collect from each sample collection vessel a particulate fraction and/or a liquid fraction.

In another aspect, in accordance with the teachings herein, the present disclosure provides, in at least one aspect, in at least one embodiment, a use of a settled particulate fraction and/or a liquid fraction collected using the openable container comprising a fluid sampling system according to the present disclosure to assay a chemical or biological parameter therein.

Other features and advantages or the present disclosure will become apparent from the following detailed description. It should be understood, however, that the detailed description, while indicating preferred implementations of the present disclosure, is given by way of illustration only, since various changes and modification within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. Like numerals designate like or similar features throughout the several views possibly shown situated differently or from a different angle.

Thus, by way of example only, part 102 in FIG. 1, FIG. 3, FIG. 4, and FIG. 5 refers to a container in each of these figures. The figures are not intended to limit the present disclosure.

FIG. 8A is a schematic view of an example embodiment of a sample collection vessel configuration of a sampling system for the collection of particulate fluids.

FIG. 8B is a perspective view of the portion labeled 8B of the sample collection vessel configuration depicted in FIG. 8A.

FIG. 8C is a schematic view of the portion labeled 8C of the sample collection vessel configuration depicted in FIG. 8A, in two different states s1 and s2.

Figure 1:
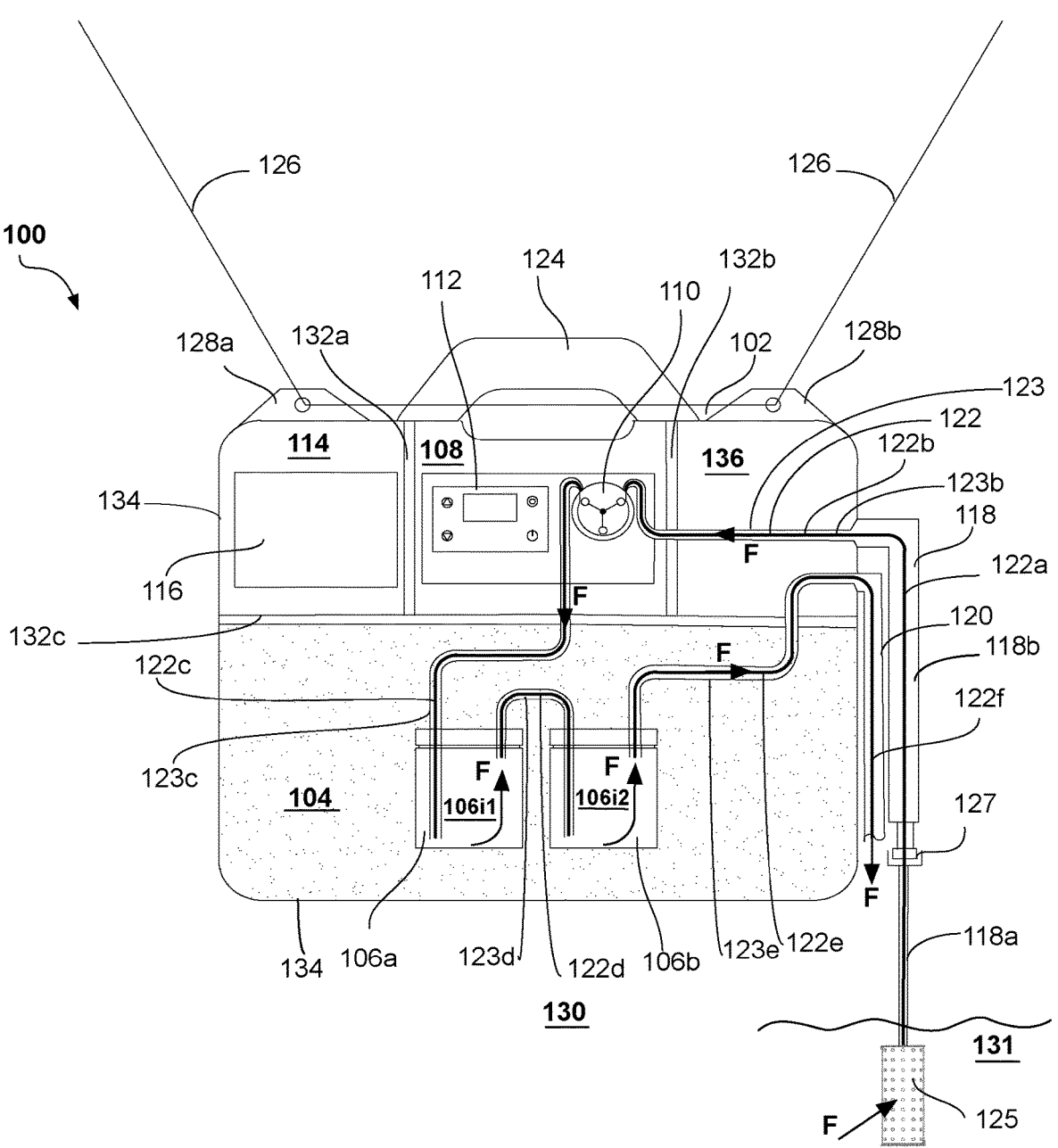
FIG. 1 is a schematic of an example embodiment of a sampling system for the collection of particulate containing fluids.

The figures together with the following detailed description make apparent to those skilled in the art how the disclosure may be implemented in practice.

DETAILED DESCRIPTION

Various processes, systems and compositions will be described below to provide at least one example of at least one embodiment of the claimed subject matter. No embodiment described below limits any claimed subject matter and any claimed subject matter may cover processes, systems, or compositions that differ from those described below. The claimed subject matter is not limited to any process, system, or composition having all of the features of processes, systems, or compositions described below, or to features common to multiple processes, systems, or compositions described below. It is possible that a process, system, or composition described below is not an embodiment of any claimed subject matter. Any subject matter disclosed in processes, systems, or compositions described below that is not claimed in this document may be the subject matter of another protective instrument, for example, a continuing patent application, and the applicants, inventors or owners do not intend to abandon, disclaim or dedicate to the public any such subject matter by its disclosure in this document.

As used herein and in the claims, the singular forms, such as "a", "an" and "the" include the plural reference and vice versa unless the context clearly indicates otherwise. Throughout this specification, unless otherwise indicated, the terms "comprise," "comprises" and "comprising" are used inclusively rather than exclusively, so that a stated integer or group of integers may include one or more other non-stated integers or groups of integers. The term "or" is inclusive unless modified, for example, by "either". The term "and/or" is intended to represent an inclusive or. That is "X and/or Y" is intended to mean X or Y or both, for example. As a further example, X, Y and/or Z is intended to mean X or Y or Z or any combination thereof.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as being modified in all instances by the term "about" The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by the context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes any number from 1 to 5 such as, but not limited to 1, 1.5, 2, 2.75, 3, 3.90, 4, and 5, for example). Similarly, other terms of degree such as "substantially" and "approximately" as used herein mean a reasonable amount of deviation of the modified term such that the end result is not significantly changed. These terms of degree should be construed as including a deviation of the modified term, such as up to 15% for example, if this deviation would not negate the meaning of the term it modifies.

Several directional terms such as "above", "below", "lower", "upper", "inner" and "outer" are used herein for convenience including for reference to the drawings. In general, the terms "upper", "above", "upward" and similar terms are used to refer to an upwards direction or upper portion in relation to a sample collection vessel generally standing upright, or a container holding the sample collection vessel while the sample collection vessel is generally standing upright, for example, such as shown for the orientation shown in FIG. 1.

Figures 6A, 6B:
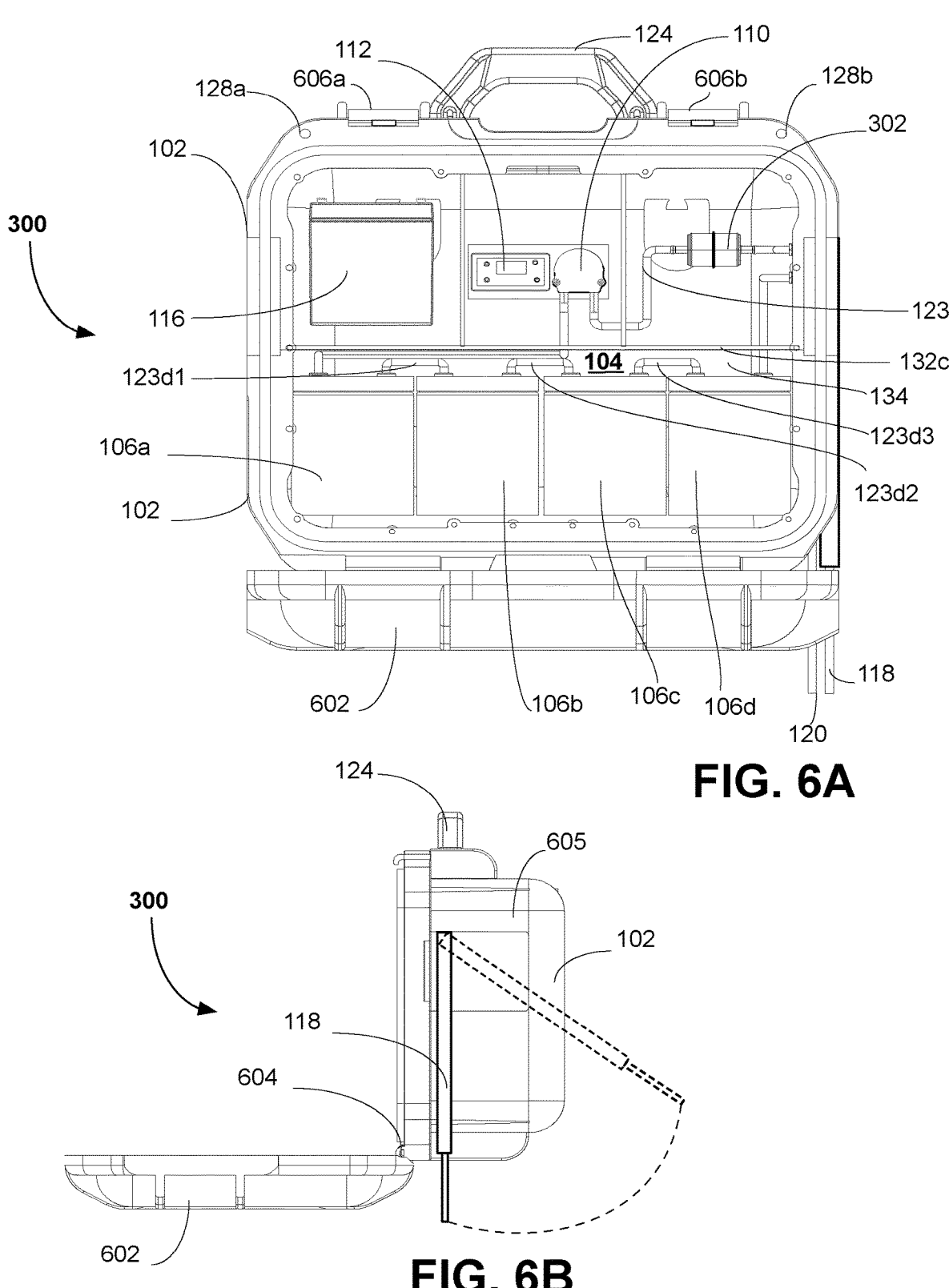
FIGS. 6A and 6B are front and side views, respectively, of the example embodiment of FIG. 4 of a sampling system for the collection of particulate fluids contained in a container shown in open position.
Figures 6C, 6D:
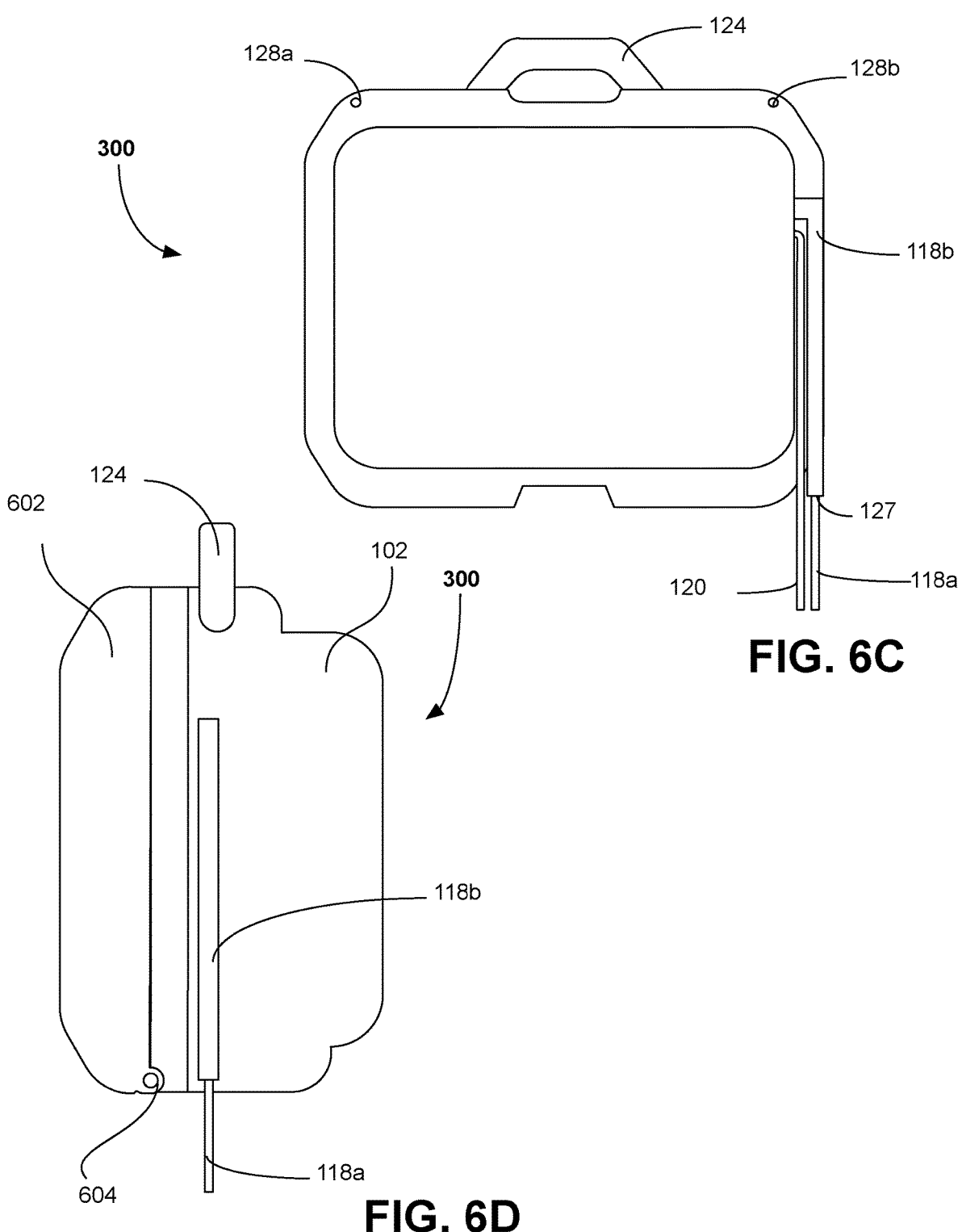
FIGS. 6C and 6D are front and side views, respectively, of the example embodiment of FIG. 4 of a sampling system for the collection of particulate fluids contained in a container shown in closed position.

Similarly the terms "lower", "below", "downward", and "bottom" are used to refer to a downwards direction or a lower portion in relation to a sample collection vessel generally standing upright, or a container holding the sample collection vessel while the sample collection vessel is generally standing upright, for example, such as shown for the orientation shown FIG. 1. Furthermore, the terms "front", "front view", and similar terms, refer to a view from a vantage point directed towards a container positioned such as shown in FIG. 6A.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present teachings herein, which is defined solely by the claims.

All publications, patents, and patent applications referred to are herein incorporated by reference in their entirety to the same extent as if each individual publication, patent or patent application was specifically indicated to be incorporated by reference in its entirety.

In general, the various embodiments of the fluid sampling system of the present disclosure can be used to collect a fluid sample, notably a fluid sample containing particulate matter suspended therein.

In broad terms, the fluid sampling system includes a container configured for the flow of particulate containing fluid therethrough. The particulate containing fluid can enter the container from the exterior through a fluid inlet and flow along or through a fluid flow path which travels through at least two serially fluidically coupled sample collection vessels, which are releasably installed in the container. Fluid flow through the flow path is controlled by a fluid pump in a manner that allows for the sequential receipt of the particulate containing fluid in the sample collection vessels, and for the particulates to settle in the sample collection vessels. Upon receipt and settlement of the particulates in the sample collection vessels, the container can then be opened, and at least one of the sample collection vessels can be releasably removed from the container.

In conventional systems which receive fluid samples containing particulate matter, the presence of the particulate matter in the fluids represents an analytical challenge as the particulate matter can interfere with assaying of the fluid sample. However, the sampling system of the present disclosure allows for sampling of particulate containing fluids while reducing interference from particulate matter in a subsequent assay. In particular, the sampling system can yield samples contained in sample collection vessels. The samples are fractionated into fluid and solid fractions, each of which can be assayed for biological or chemical parameters.

Furthermore, since the sampling system of the present disclosure includes a fluid pump coupled to a controller, the system can be conveniently deployed at a sampling site, and, in an aspect, samples can be collected at specific times, by operating the fluid pump with the controller according to a specified sampling time sequence.

In what follows selected example embodiments are described with reference to the drawings.

Figures 2A, 2B, 2C, 2D, 2E, 2F:
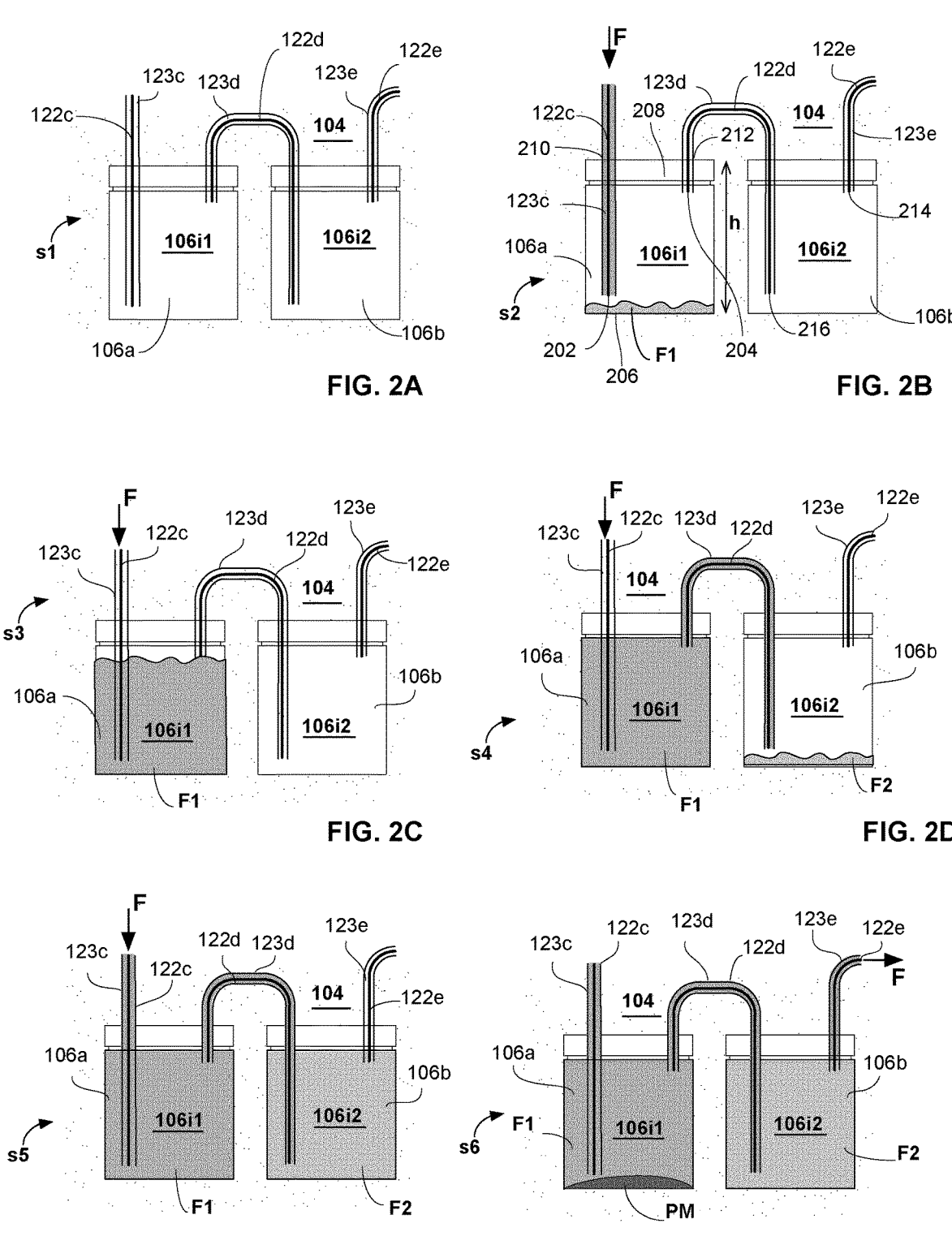
FIGS. 2A-2F are schematic views of two example serially fluidically coupled sample collection vessels in first, second, third, fourth, fifth and sixth states, respectively.
Figure 3:
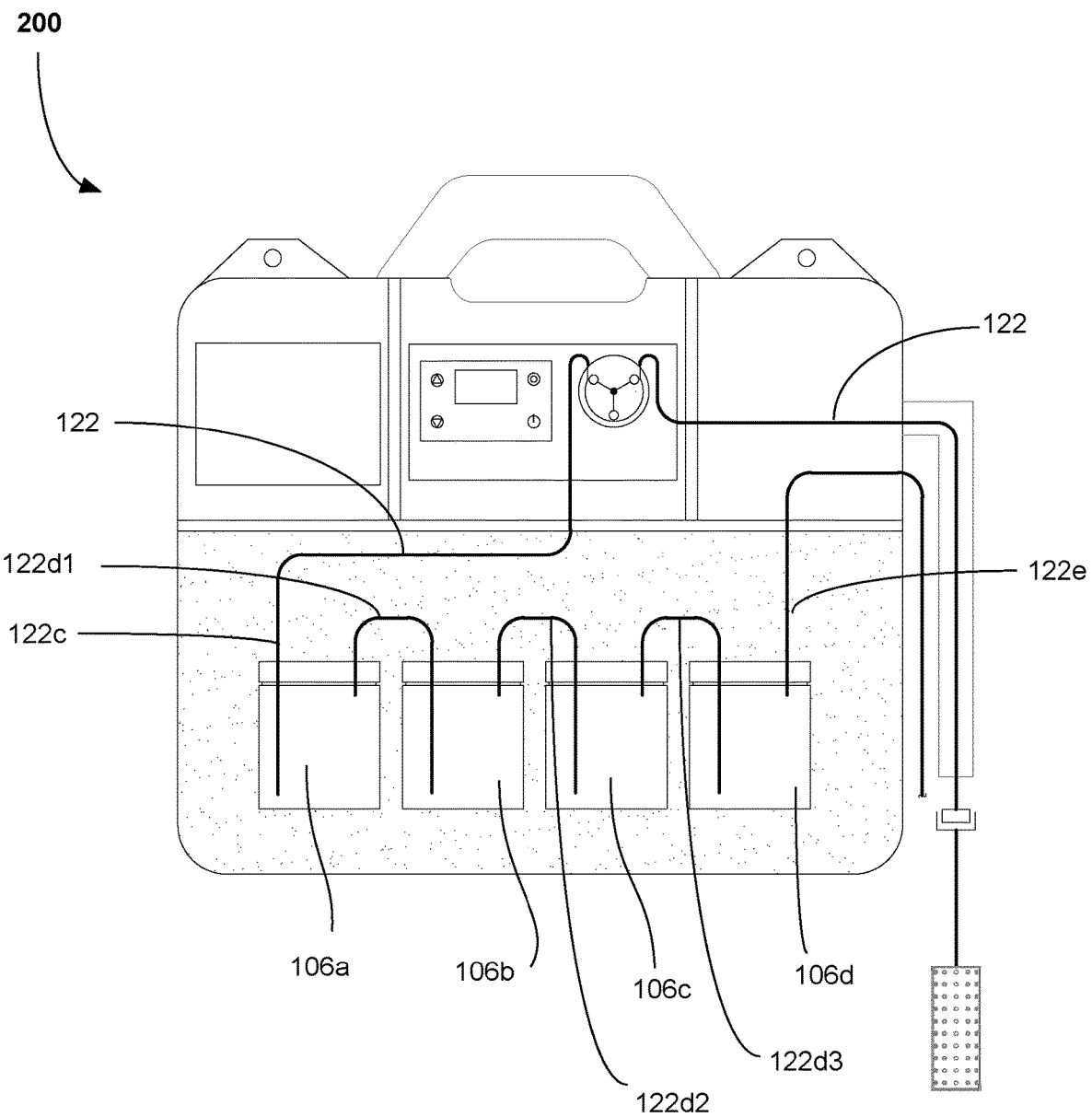
FIGS. 3 to 5 are schematics of other example embodiments of a sampling system for the collection of particulate containing fluids.
Figure 4:
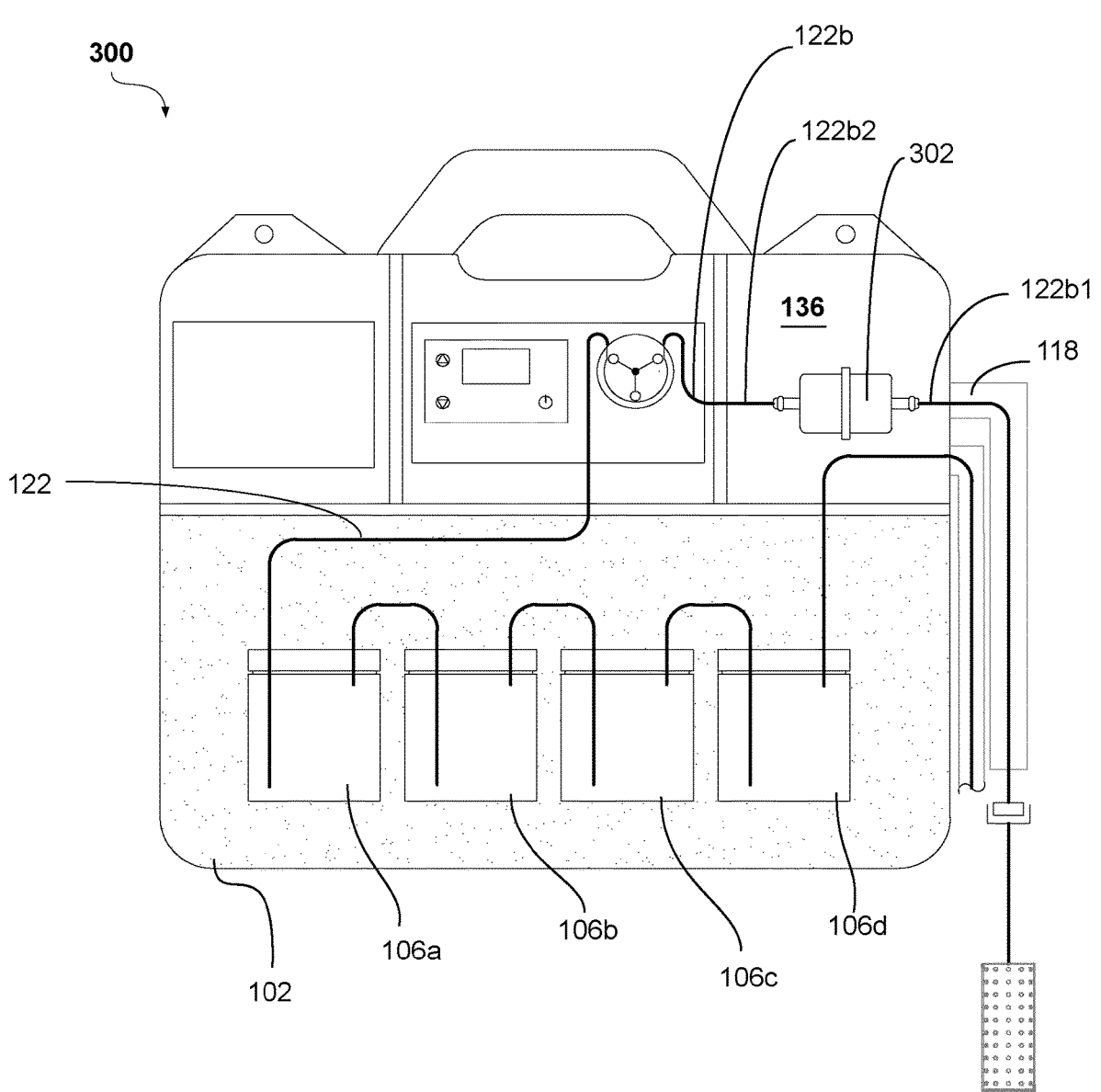
Figure 5:
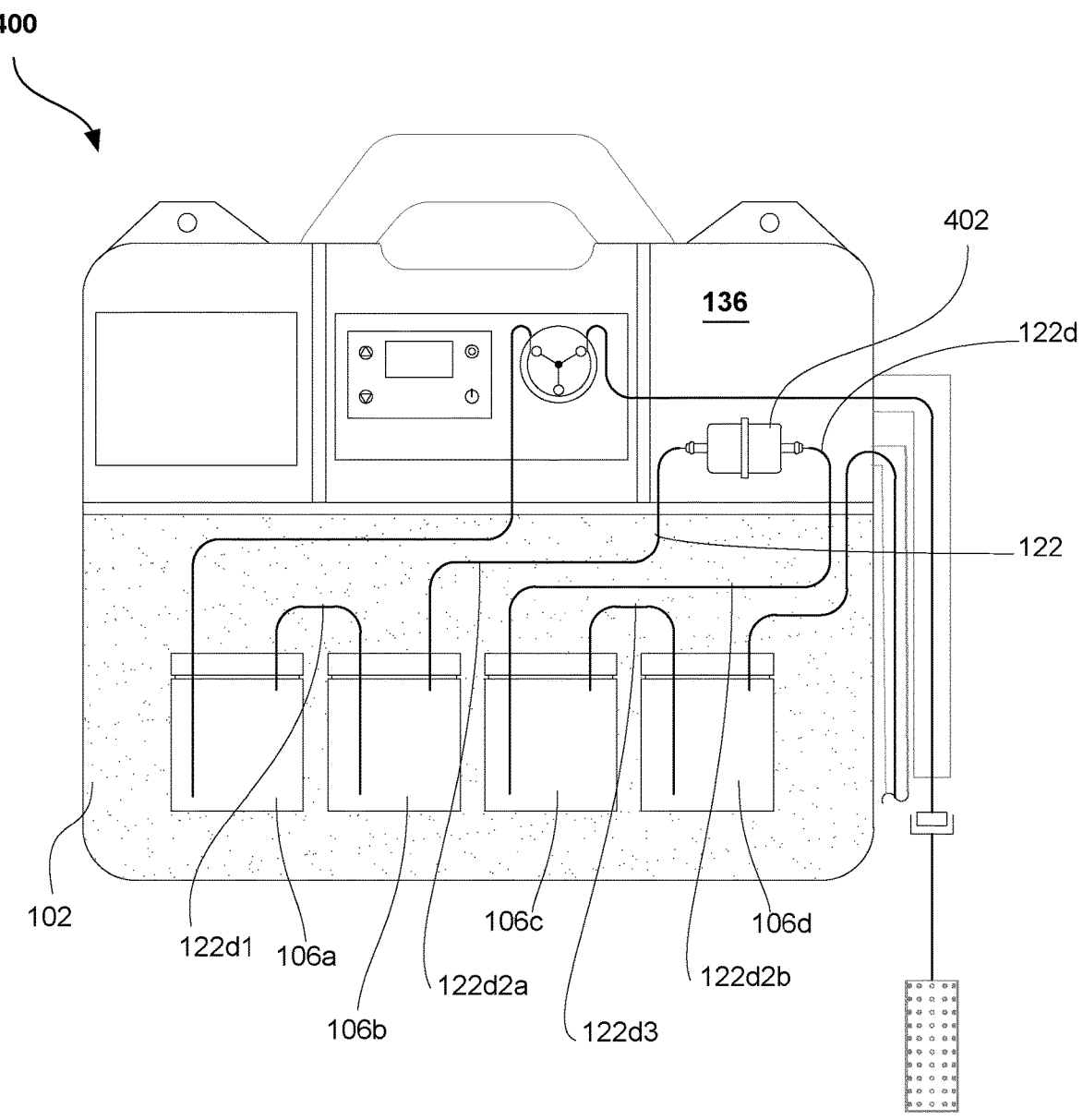

In general overview, FIG. 1 shows a first example embodiment of a schematic of a sampling system 100 for the collection of particulate containing fluids. FIGS. 2A-2F show two serially fluidically coupled sample collection vessels of sampling system 100 in a first, second, third, fourth, fifth and sixth states, respectively. FIG. 3 shows a second example embodiment of a schematic of a sampling system 200 for the collection of particulate containing fluids. FIG. 4 shows a third example embodiment of a schematic of a sampling system 300 for the collection of particulate containing fluids. FIG. 5 shows a fourth example embodiment of a schematic of a sampling system 400 for the collection of particulate containing fluids. FIGS. 6A-6D show several views of an example embodiment of a sampling system 300. FIGS. 7A-7D show flow charts of example embodiments of methods 700, 701, 702 and 703 for collecting samples using the sampling system 200 of FIG. 3, in accordance with the teachings herein. FIGS. 8A-8C show an example configuration 800 of two serially connected sample collection vessels, notably a configuration wherein the sample collection vessels include a detachable filter disposed therein.

Referring initially to FIG. 1, shown therein is a schematic of an example embodiment of a sampling system 100 for the collection of particulate containing fluids. Sampling system 100 includes openable container 102 (shown in an opened position) comprising interior compartments 104, 108, 114 and 136 formed by outer container wall 134 and inner compartment walls 132a, 132b and 132c. Openable container 102 further includes hand grip 124 formed by a central upper portion of openable container 102 to allow for transport of openable container 102. Linking portions 128a and 128b, formed by upper portions of openable container 102, are located so that they are laterally offset relative to both sides of handgrip 124. Linking portions 128a and 128b may be attached to suspension arrangement 126 in some cases. Thus, openable container 102 can be suspended thereby allowing for the implementation of certain operational aspects of sampling system 100, as further hereinafter described. When in a closed position, most preferably openable container 102 is substantially water tightly sealed, so that when container 102 is suspended in a fluid in a closed position, fluid which is in contact with the exterior of the container 102, does not enter interior compartments 104, 108, 114 or 136. When in an opened position the contents of openable container 102, notably sample collection vessels 106a and 106b housed in interior compartment 104, can be accessed and removed from the container. It is to be understood that in general, the term "openable container", as used herein, refers to a container which may be opened and closed, using any means for opening and closing the container. In this respect, example embodiment 100, includes a hinged lid (as hereinafter further described with reference to FIGS. 6A-6D). However, in other embodiments other means of opening and closing the container (e.g., a sliding lid, a snap-and-lock lid etc.) may be constructed.

Continuing to refer to FIG. 1, and turning to interior compartments, 104, 108, 114 and 136, interior compartment 104 is arranged to house sample collection vessels 106*a* and 106*b*. Interior compartment 108 is arranged to house peristaltic fluid pump 110 and controller 112. Controller 112 is operably coupled to peristaltic fluid pump 110 to control peristaltic fluid pump 110. Furthermore, controller 112 and peristaltic fluid pump 110 are each electrically coupled to and powered by battery 116 housed in interior compartment 114. Battery 116 can be any battery suitable to power controller 112 and peristaltic fluid pump 110, and in general is selected to be compatible with the physical dimensions of openable container 102, and notably interior compartment 114, while providing the desired power. Thus, for example, battery 116 can be a 12 Volt battery. Battery 116 can further be a rechargeable or non-rechargeable battery, including a battery that is rechargeable by renewable energy sources, such a solar power, wind power, geothermal power, or vibrational power, for example. In further alternate embodiments, the fluid pump 110 may be powered by an electric power transmission system providing alternating current (AC) or direct current (DC). In the example embodiment shown in FIG. 1, interior compartment 136 is empty, but for a portion 123*b* of fluid conduit 123, however in other embodiments (see: embodiments 300 and 400 in FIG. 4 and FIG. 5 below, respectively, for example) interior compartment 136 can additionally house a filtering device.

Controller 112 can be implemented using a suitable controller that includes at least one processor, memory, as well as hardware for sending and receiving signals including an analog to digital convertor (ADC), a digital to analog converter (DAC) and a communication unit that includes a wireless radio, and optionally a USB port. The DAC can be used to convert digital control signals to analog control signals, such as signals to control the pump flow rate, to the fluid pump 110 and also optionally a cooling system for embodiments which include the cooling system. The ADC can be used to digitize analog measurement signals such as an analog temperature signal provided by the cooling system for embodiments which include the cooling system, as well as signals from environmental sensors (not shown), which, in some embodiments, may be used by the processor to control activation of the fluid pump 110. The wireless radio can be used for receiving control signals from a remote device that may be used to remotely control the operation of the fluid pump 110, and optionally the cooling system, and optionally environmental sensors.

The memory can be implemented using ROM or RAM and comprises software that includes program instructions, which when executed by a processor of the controller 112, configures the controller 112 to operate in a new, specific and predefined manner for controlling the fluid pump 110 in accordance with the teachings herein, and optionally with a cooling system that has a settable thermostat so that the controller 112 can control the temperature of the container 102 that includes sample collection vessels.

The software may be implemented using high-level procedural language and/or firmware. The high-level procedural language may be C, C++ or any other suitable programming language and may comprise modules or classes, as is known to those skilled in object-oriented programming. The firmware software may be written in some form of assembly of machine language. The program code may be preinstalled and embedded during manufacture and/or may be later installed as an update for an already deployed controller. The medium may be provided in various forms, including non-transitory forms such as, but not limited to, one or more diskettes, compact disks, tapes, chips, USB keys and magnetic and electronic storage. In alternative embodiments, the medium may be transitory in nature such as, but not limited to, wire-line transmissions, satellite transmissions, Internet transmissions (e.g., downloads), media, digital and analog signals, and the like. The computer useable instructions may also be in various formats, including compiled and non-compiled code.

Openable container 102 further includes fluid inlet 118 and fluid outlet 120, each traversing outer container wall 134 and extending to be in fluid communication with exterior 130 of the container 102. Fluid inlet 118 includes first portion 118*a* and second portion 118*b*. Second portion 118*b* traverses outer container wall 134 and is fluidically coupled to first portion 118*a* via flexible coupling 127. Thus, first portion 118*a* represents a further extension into exterior 130. Furthermore, the end portion of first portion 118*a* of fluid inlet 118 may include mesh filter 125. Mesh filter 125 may have a mesh size ranging from about 0.5 mm to about 2.0 mm, and may be, for example, a tubular stainless steel filter that is about 10 cm to 25 cm long having a mesh size (i.e., size of the openings in the mesh) of about 1.0 mm. Mesh filter 125 prevents the entry and flow of debris and larger size organic material through fluid inlet 118. The fluid path from fluid inlet 118 to fluid outlet 120 is fluidically coupled to fluid conduit 123, comprising fluid conduit portions 123*b*, 123*c*, 123*d* and 123*e*. Fluid inlet 118 and fluid outlet 120 together with interiors 10611 and 10612 of serially fluidically connected sample collection vessels 106*a* and 106*b*, respectively, are portions of fluid path 122 for fluid flow F through openable container 102. In this respect, fluid path 122 is formed by: fluid path portion 122*a*, corresponding with fluid inlet 118; fluid path portion 122*b* corresponding with fluid conduit portion 123*b* running from fluid inlet 118 to peristaltic fluid pump 110; fluid path portion 122*c* corresponding with fluid conduit portion 123*c* running from peristaltic fluid pump 110 to interior 10611 of the interior of sample collection vessel 106*a*; fluid path portion 122*d* corresponding with fluid conduit portion 123*d* which runs from interior 10611 of the interior of sample collection vessel 106*a* to interior 10612 of the interior of sample collection vessel 106*b*, and serially connects sample collection vessel 106*a* and sample collection vessel 106*b*; fluid path portion 122*e* corresponding with fluid conduit portion 123*e* running from interior 10612 of the interior of sample collection vessel 106*b* to fluid outlet 120; and fluid path portion 122*f*, corresponding with fluid outlet 120. Together fluid inlet 118, fluid conduit 123, and serially fluidically coupled sample collection vessels 106*a* and 106*b* are configured and fluidically coupled so that fluid can flow from fluid inlet 118 through fluid path 122 through openable container 102 to fluid outlet 120. In general, fluid can be caused to flow through fluid path 122 by fluidically coupling fluid inlet 118, notably first portion 118*a* thereof, to a fluid source 131 situated in exterior 130 and activating peristaltic fluid pump 110 through controller 112.

Next, fluid flow and collection of sample materials with particular reference to sample collection vessels 106*a* and 106*b* will be discussed. Referring now to FIG. 2A to FIG. 2F (in conjunction with FIG. 1), shown therein are two serially coupled sample collection vessels 106*a* and 106*b*, situated in compartment 104 in openable container 102, in six different states, including first state s1 (FIG. 2A), second state s2 (FIG. 2B), third state s3 (FIG. 2C), fourth state s4 (FIG. 2D), fifth state s5 (FIG. 2E) and sixth state s6 (FIG. 2F). States s1, s2, s3, s4, s5 and s6 occur at successively different time points, i.e., first state s1 occurs at a first time point. Second state s2 corresponds with a second time point occurring later than the first time point. Third state s3 corresponds with a third time point occurring later than the second time point, and so forth. Sampling system 100 is positioned so that fluid inlet 118 is fluidically coupled to sample fluid source 131 (as shown in FIG. 1) during states s1 to s6.

Referring to FIG. 2A, at first state s1, collection vessels 106a and 106b are empty, and, as such, state s1 reflects a time prior to initiation of sampling from fluid source 131, i.e., a time prior to activation of peristaltic fluid pump 110. Upon activation of peristaltic fluid pump 110, fluid from fluid source 131 will enter openable container 102 via fluid inlet 118. It is noted, that, in general, controller 112 includes a software module with software instructions for setting and controlling the activation and deactivation time for peristaltic fluid pump 110. The activation and deactivation time thus can be set by an operator of sampling system 100 prior to installing sampling system 100 for fluid sampling. In other embodiments, controller 112 may include a wireless communication unit, such as a wireless receiver (i.e., wireless radio) that is operable to receive a signal from a remotely located device, such as a smart phone, a tablet or desktop computer, that is configured to control controller 112 to thereby allow activation and deactivation of peristaltic fluid pump 110. Thus, it will be clear that controller 112 and peristaltic fluid pump 110 are operably connected to one another as well as the fluid path 122 including inlet 118, fluid conduit 123 and serially fluidically coupled sample collection vessels 106a and 106b, and that controller 112 can be provided, e.g., via software instructions, with activation and deactivation times for predefined sampling intervals or receive control signals remotely for activation and deactivation thereby allowing for installment of sampling system 100 at any suitable sample location for sampling fluids, and once installed, sampling system 100 may be used to collect a fluid sample, at a suitable time, as desired through operation of the controller 112.

Referring next to FIG. 2B, at second state s2, a quantity of fluid has been pumped by peristaltic fluid pump 110 from fluid source 131 into openable container 102 and fluid has flown through fluid path sections 122a, 122b and 122c, to reach interior 106i1 of sample collection vessel 106a. It is noted that fluid conduit portion 123c traverses top portion 208 of sample collection vessel 106a through an aperture 210 in top portion 208 of sample collection vessel 106a. Furthermore, fluid conduit portion 123d traverses top portion 208 of sample collection vessel 106a through another aperture 212 in top portion 208 of sample collection vessel 106a. Fluid outlet 202, formed by the bottom portion of fluid conduit portion 123c, is positioned closely to the bottom portion 206 of sample collection vessel 106a. Thus, for example, fluid outlet 202 may be separated from the bottom of sample collection vessel 106a by 2 cm, 1 cm, 0.5 cm or less. By contrast, fluid inlet 204 formed by a bottom portion of fluid conduit portion 123d is positioned closely to the top portion 208 of sample collection vessel 106a. Thus, for example, fluid inlet 204 may be separated from the top of sample collection vessel 106a by 2 cm, 1 cm, 0.5 cm or less. The configuration (e.g., location and dimensions) of fluid outlet 202 and fluid inlet 204, in an aspect hereof, allows filling of sample collection vessel 106a to its full capacity (as shown in FIG. 2D). Furthermore, in an aspect hereof, the configuration of fluid outlet 202 and fluid inlet 204 generally limits contact of the received fluid with the air in the sample collection vessels, which reduces the occurrence of oxidation reactions thereby potentially altering sample constituents, since fluid is received at the bottom portions of sample collection vessels 106a and 106b, and following initial receipt of a small quantity of fluid, fluid inlet 204 becomes submerged, as more fluid is received in sample collection vessels 106a or 106b. At the same time, the configuration permits for mixing and homogenization of the fluid in sample collection vessel 106a, as sample collection vessel 106a gradually fills. Furthermore, in an aspect hereof, the configuration of fluid outlet 202 and fluid inlet 204 reduces the transfer of solids from sample collection vessel 106a to 106b since solids are received at the bottom portion of sample collection vessel 106a where particulate matter (PM) sediments form (see: FIG. 2F). In different embodiments, the configuration and relative positions of fluid outlet 202 and fluid inlet 204 may be varied, however in preferred embodiments, fluid conduit portion 123c extends downwards into sample collection vessel 106a to approximately bottom portion 206 of sample collection vessel 106a. Fluid conduit portion 123d extends downwards into sample collection vessel 106a extending downwards therefrom no further than to approximately half the height (h) of sample collection vessel 106a, and, more preferably, even closer to top portion 208 of sample collection vessel 106a, such as extending into sample collection vessel 106a, for example, approximately one quarter of the height (h) of sample collection vessel 106a, or even less. It is noted that fluid inlet 216 and fluid outlet 214 in sample collection vessel 106b are configured similarly as fluid inlet 202 and fluid outlet 204.

Referring next to FIG. 2C, at third state s3, as pumping of fluid from fluid source 131 has continued, the fluid level in sample collection vessel 106a has risen to fill most of interior 106I1 of fluid sample collection vessel 106a.

Referring next to FIG. 2D, at fourth state s4, as pumping of fluid from fluid source 131 has further continued, interior 106I1 of sample collection vessel 106a is entirely filled, and fluid has flown through fluid path section 122d towards sample collection vessel 106b to reach interior 106I2 of sample collection vessel 106b.

Referring next to FIG. 2E, at fifth state s5, as pumping of fluid source 131 has further continued, interior 106I1 of sample collection vessel 106a and interior 106I2 of sample collection vessel have entirely filled. At fifth state s5, peristaltic fluid pump 110 may be deactivated. In this respect, controller 112 may be set to pump for a sufficiently long period of time to pump a volume of fluid source 131 that is sufficient to fill sample collection vessel 106a and 106b i.e., a volume corresponding approximately with the total volume of sample collection vessel 106a and 106b, and to deactivate more or less immediately following filling of sample collection vessel 106b. En some embodiments (not shown), sampling system 100 may not include fluid pathway section 122e and fluid outlet 120. However, in general it is deemed beneficial to include fluid path section 122e and fluid outlet 120 since this allows for potential overflow, and may not require as much accuracy in carefully controlling the pumping time.

Referring next to FIG. 2F, at sixth state s6, peristaltic fluid pump 110 has been deactivated for a period of time and particulate matter (PM) has been permitted to settle at the bottom of sample collection vessel 106a. In general, it is desirable to control the flow rate through flow path 122 so that significant quantities of particulate matter (PM) settle in sample collection vessel 106a, while limited quantities of particulate matter (PM) are conveyed to sample collection vessel 106b. In some embodiments, a significant quantity of particulate matter (PM) may be at least or up to about 75% (w/w), at least or up to about 80% (w/w), at least or up to about 85% (w/w), at least or up to about 90% (w/w), at least or up to about 95% (w/w), or at least or up to about 99% (w/w) of the total mass of particulate matter collected in sample collection vessels 106a and 106b and this significant quality of particulate matter (PM) is collected in sample collection vessel 106a, with the balance being collected in sample collection vessel 106b. In this manner, in sample collection vessel 106b a fluid sample is obtained from which a substantial quantity, substantially all or all of particulate material (PM) has been removed. It is noted that although it generally takes a certain period of time for particulate matter (PM) to settle after fluid flow through flow path 122 has stopped, portions of particulate matter (PM) present in fluid from fluid source 131 may also settle in sample collection vessel 106a prior to deactivation of peristaltic fluid pump 110. Furthermore, it will be understood by those of skill in the art that the settlement kinetics of the particulate matter (PM) depend on various variables, including, for example, the fluid flow rate through fluid flow path 122, and the constituents of fluid from the fluid source 131, including, for example, the constituents and concentration of the particulate matter (PM). Accordingly, the period of time for particulate matter (PM) to fully settle after deactivation of peristaltic fluid pump 110 may vary and can range for example from at least about 15 minutes up to about 6 hours.

It is noted that, flow rates through fluid path 122 may be controlled and adjusted by an operator of the fluid sampling systems of the present disclosure. Suitable flow rates in this respect may vary and include, for example, flow rates ranging from about 1.5 ml/sec to about 7 ml/sec. Flow rates through fluid path 122 may be controlled in a number of ways, including by varying the rotational rate of the rotor of peristaltic pump 110 through controller 112. Thus, as will be understood by those of skill in the art, at lower rotational rates, peristaltic pump 110 will provide lower flow rates. The flow rate may also be controlled by selection of the inner diameter of the flexible tube of peristaltic pump 110. As will be understood by those of skill in the art, flexible tubes having a larger inner diameter will provide a higher flow rate. Furthermore, the flow rate may be controlled by selection of pump 110. Thus, for example, some peristaltic pumps 110 may be able to provide a variable flow rate ranging from about 1.5 ml/sec to about 3 mi/sec, while other peristaltic pumps 110 may be able to provide a variable flow rate ranging from about 3 ml/sec to about 7 ml/sec. Thus, the present disclosure further includes, in some embodiments, a removable peristaltic pump 110, allowing an operator to replace pumps to thereby control flow rates through fluid path 122.

It is noted that for the sampling systems of the present disclosure, the sampling times may be varied. In some embodiments, a fluid sample is collected following a single activation and deactivation of peristaltic pump 110. This may, for example, be a suitable manner to operate a fluid sampling system according to the present disclosure when substantially no temporal variations in constituents in fluid from the fluid source 131 is occurring, or when it is desirable to exclude any temporal variations, i.e., when it is desirable to obtain a fluid sample at a specific time. Thus, in a relatively brief period, for example, a period of from about 1 to about 10 minutes following activation of peristaltic pump 110, sample collection vessels 106a and 106b may be filled. The thus collected fluid sample may be referred as a 'grab sample'.

In other embodiments, a sample is collected following multiple activations and deactivations of peristaltic pump 110. Thus, peristaltic pump 110 may be activated and deactivated multiple times during a period of time in which it is desirable to collect a fluid sample, for example, a period of 1 day, 2 days, 10 days, 1 week, or 1 month. This period of time may be referred to as the sample collection period. Thus, peristaltic pump 110 may be activated for a first period, for example, for about five 5 seconds to about 30 seconds, then be deactivated, for a first hold time interval, for example for 15 minutes to 60 minutes, then be activated a second time and deactivated for a second hold time interval, then be activated a third time and deactivated for a third hold time interval, and so on. Thus, if, by way of example only, a 30 minute hold time interval was selected, and the sample collection period is 24 hours, then activation/deactivation of peristaltic pump 110 would occur 48 times, and 48 fluid volumes would be collected during the sample collection period. It will be clear that by selecting an appropriate combination of flow rate, activation/deactivation periodicity, hold time interval, and sample collection period, sample collection vessels 106a and 106b may be filled at the end of a selected sample collection period. The collected fluid sample may be said to be representative of fluid from the fluid source 131 over the sample collection period. This embodiment may be implemented when it is desirable to limit the effects of temporal variations in fluid constitution that may occur, such as, for example, in sewer fluids in which constituents may vary depending on the time of the day, and when instead it is desirable to obtain a sample that reflects an average over a certain time period. Samples collected following multiple activations and deactivations of peristaltic pump 110 may be referred to as 'composite samples'.

In one embodiment, the controller can be coupled to an environmental sensor (not shown) capable of detecting a change in an environmental parameter related to exterior 130 of the container 102, and the controller 112 can be configured to activate the fluid pump 110 upon the detection of a change in an environmental parameter by the sensor. Such a change in the environment can, for example, be a weather change, or a change in a parameter in the fluid source 131, or any other physical condition in the environment. Thus, for example, the environmental sensor can be a rain sensor, a temperature sensor, a pH sensor, a turbidity sensor, a biochemical oxygen demand (BOD) sensor, a chemical oxygen demand (COD), an electrical conductivity (EC) sensor, or a total dissolved solids (TDS) sensor. The environmental sensor may be installed in close proximity of the sample collection system, and may, for example, be attached to the exterior of openable container 102, or the sensor may be more remotely installed and coupled to the controller 112 by, for example, a wireless sensor network (WSN) connection. This embodiment of the sampling system of the present disclosure permits the collection of a sample when a change occurs in an environmental parameter, and thus the effect of the change in environmental parameter on the constitution of source fluid may be evaluated, notably by evaluating and comparing samples collected prior to and following a change in the environmental parameter.

It is further noted that in some embodiments, the sample collection period and flow rate, activation/deactivation periodicity, hold time interval, and sample collection period, may be selected so that a specific sample volume (e.g., 1 liter, 2 liters) is collected in sample vessels 106a and 106b. Upon completion of sampling, sample vessels 106a and 106b may be filled or partially filled, depending on the volumes of sample vessels 106a and 106b. In other embodiments, the sample collection period and flow rate, activation/deactivation periodicity, hold time interval, and sample collection period, may be selected so that sampling is performed during a specific sample collection period (e.g., 24 hrs). Again, sample vessels 106a and 106b may be filled or partially filled, depending on the volumes of sample vessels 106a and 106b and the amount of fluid which is sampled.

It is clear however that when operating peristaltic pump 110, the activation/deactivation periodicity, the hold time interval, the sample collection period, and the flow rate, in accordance herewith may all be selected and controlled as desired.

Upon settlement of the particulate matter (PM) in sample collection vessel 106a, openable container 102 may be retrieved and opened to release sample collection vessels 106a and 106b from openable container 102, for assaying of the contents of the sample collection vessels 106a and 106b. In this respect, it is noted that both the liquid fraction and the solid, settled particulate matter fraction (PM), may be separately recovered from sample collection vessel 106a, for example, by decanting the liquid fraction from sample collection vessel 106a in an additional vessel, and then separately removing the solid, settled particulate matter (PM) fraction from sample collection vessel 106a. Each of the fractions recovered from sample collection vessel 106a, as well as the liquid fraction recovered from sample collection vessel 106b, may subsequently be assayed, for example, for chemical or biological parameters.

To briefly recap, various embodiments of a fluid sampling system comprising a container configured for the flow of particulate containing fluid therethrough have been provided. In an example embodiment, the particulate containing fluid can enter container 102 from an exterior fluid source 131 through fluid inlet 118 and can flow through fluid flow path 122, including two serially fluidically coupled sample collection vessels 106a and 106b. Fluid flow through flow path 122 is controlled by a peristaltic fluid pump 110 in a manner that allows sequential receipt of the sampled fluid in the first and second sample collection vessels 106a and 106b, and for particulates to settle in the first sample collection vessel 106a. Upon receipt and settlement of the particulates in the first collection vessel 106a, the container 102 can be retrieved and opened and sample collection vessels 106a and 106b can be released from container 102.

Next, other selected example embodiments of sampling systems provided in accordance with the present disclosure will be discussed.

Referring next to FIG. 3, shown therein is an alternate embodiment of a fluid sampling system 200 which includes four sample collection vessels 106a, 106b, 106c and 106d. Fluid path 122 includes fluid path portions 122d1, 122d2 and 122d3. It is noted that for purposes of clarity, in the schematic view on FIG. 3 fluid path 122 is shown, while no fluid conduits are shown. It is to be understood, however, that fluid path 122 is formed by fluid conduits, similar to fluid conduit 123 shown in FIG. 1, and further as shown in FIG. 6A. Example sampling system 200 allows for the collection of larger sample volumes than example system 100 since there are more sample collection vessels 106a to 106d that are each of similar size as the sample collection vessels 106a and 106b used in sampling system 100, although in other embodiments different sized sample collection vessels may be used. Furthermore, sampling system 200 can facilitate fluid sampling of fluids with higher concentrations of particulate matter (PM). Thus, notably in instances where the concentration of particulate matter (PM) is sufficiently high in the fluid obtained from the fluid source 131 so that not all or substantially all particulate matter settles in sample collection vessel 106a, with the sampling system 200, and instead fluid containing some quantity of particulate matter is also transferred to sample collection vessel 106b, and possibly even onwards to sample collection vessel 106c, and therefore further quantities of particulate matter (PM) may settle in sample collection vessels 106b and, optionally in sample collection vessel 106c. The distribution of relative quantities of particulate matter (PM) across the four sample collection vessels may vary, as will generally be clear based on the discussion herein with respect to FIGS. 2A-2F. In some embodiments, the final sample collection vessel (i.e., sample collection vessel 106d in FIG. 3) can contain less than about 5% (w/w), less than about 4% (w/w), less than about 3% (w/w), less than about 2% (w/w), or less than about 1% (w/w) of the total amount of particulate matter collected in all sample collection vessels (i.e., sample collection vessels 106a, 106b, 106c and 106d in FIG. 3), with the balance of the particulate matter being collected in the other sample collection vessels (i.e., sample collection vessels 106a, 106b and 106c in FIG. 3). For example, in some cases, the first sample collection vessel (La, sample collection vessel 106a in FIG. 3) can contain from at least up to about 25% (w/w), up to about 50%, up to about 60%, up to about 65%, up to about 70%, or up to about 75% (w/w) of the total amount of particulate matter collected in all sample collection vessels (La, sample collection vessels 106a, 106b, 106c and 106d in FIG. 3), with the balance of the particulate matter being collected in the other sample collection vessels (i.e., sample collection vessels 106b, 106c and 106d in FIG. 3). As herein before noted, and as will be understood by those of skill in the art, the settlement kinetics and relative distribution across the sample collection vessels of the particulate matter (PM) depend on various variables, including, for example, the fluid flow rate through fluid flow path 122, and the constituents of the fluid from fluid source 131, including, for example, the constituents and concentration of the particulate matter (PM). It is noted that in further alternative embodiments of the sampling systems described in accordance with the teachings herein, there may be various numbers of sample collection vessels, including three, five, six, seven, eight, or more sample collection vessels (not shown). Furthermore, the volume of the sample collection vessels in different embodiments, may vary, and may range, for example, from about 50 ml vessels to about 4 liter vessels. It will be understood, therefore that in different embodiments of the fluid sampling system of the present disclosure, the total maximum collectable sample volume may range, for example, from about 100 ml (e.g., in an embodiment including two 50 ml sample collection vessels) to about 32 liters (e.g., in an embodiment including eight 4 liter sample collection vessels), and thus, the total maximum collectable sample volume may, in different embodiments of the fluid sampling system, for example, be about 100 ml, 500 ml, 1 liter, 2 liter, 5 liter, 10 liter, 12 liter 15 liter, 20 liter, 24 liter, 30 liter, 32 liter, or more.

Referring next to FIG. 4, shown therein is an alternative embodiment of a fluid sampling system 300 which includes four sample collection vessels 106a, 106b, 106c and 106d, and which further includes, disposed in fluid path 122, filter 302 housed in compartment 136. In particular, filter 302 is disposed in fluid path portion 122b, wherein filter 302 together with fluid path portions 122b1 and 122b2 forms fluid path portion 122b. Thus fluid upon entering openable container 102 via fluid inlet 118 initially traverses filter 302 before flowing through fluid path 122 towards sample collection vessel. 106a. Filter 302 can, for example, be a filter having a pore size of from about 0.25 μm to about 5 μm, for example, a pore size of about 0.45 μm. The pore size may be selected based on the particulate containing fluid being collected. In general, the pore size can be selected to be sufficiently large to prevent clogging of filter 302 during the period of time sample fluid is being collected in sample collection vessels 106a and 106b, and sufficiently small to trap at least a modicum of particulate matter (PM). Thus, where the fluid contains larger size particulates, filter 302 generally can be selected to have a matching larger pore size. For example, when the particulate containing fluid contains particulates sized to have an average particulate size of about 1 μm, the filter size can be selected to be between about 1 μm and about 1.2 μm so that at least a quantity of the particulates can be trapped by filter 302. It is noted that where municipal wastewater is assayed, in general the pore size of filter 302 can be selected to be in a range of between about 0.3 μm and about 0.6 μm, for example, about 0.45 μm. Filters may be fabricated from different materials, including for example, polyethersulfone (PES) or polyvinylidene fluoride (PVDF). Furthermore it is noted that filter 302 is preferably releasably installed in compartment 136. Upon completion of the sampling, filter 302 may be released (i.e., removed) and the fluid source material retained within the filter 302 may be analyzed, for example, for the presence of chemical and biological entities therein.

Referring next to FIG. 5, shown therein is an alternate embodiment of a fluid sampling system 400 which includes four sample collection vessels 106a, 106b, 106c and 106d, and which further includes, disposed in fluid path 122, filter 402 housed in compartment 136. In particular, filter 402 is disposed in fluid path portion 122d, wherein filter 402 together with fluid path portions 122d2a and 122d2b forms fluid path portion 122d2. Thus fluid upon entering openable container 102 via fluid inlet 118 flows through fluid path 122 through sample collection vessels 106a and 106b, and then traverses filter 402 before flowing towards sample collection vessels 106c and 106d. Filter 402 may be similar to filter 302 and can, for example, be a filter having a pore size of from about 0.25 μm to 1 μm, for example, a pore size of about 0.45 μm. Furthermore it is noted that filter 402 is preferably releasably installed in compartment 136. Filter 402 may be removed after sample fluid has been collected and the fluid source material retained within the filter 402 may be analyzed, for example, for the presence of certain chemical and biological entities therein using known analytical techniques.

Continuing to refer to FIG. 5, it is furthermore noted that the disposition of filter 402 within fluid path portions 122d2a and 122d2b of fluid path 122 allows for a further filtering step to remove fine particulate matter (PM) which has not settled in sample collection vessels 106a and 106b. Such fine particulate matter generally has a size less than about 1 μm, less than about 0.75 μm, less than about 0.5 μm, less than about 0.25 μm, or less than 0.1 μm. Further removal of particulate matter (PM) may be desirable when subsequent assaying of the liquid sample collected in sample collection vessels 106a and 106b involves assaying techniques in which the presence of particulates may interfere with the assaying technique. Thus, for example, where the collected liquid sample subsequently is subjected to mass spectrometry, liquid chromatography mass spectrometry-mass spectrometry (LC-MS/MS), or to liquid chromatography quadrupole time-of-flight (LC-QTOF), as may be the case, for example, when assaying for constituents having a low n-octanol water/partition coefficient (KoW), such as in many pharmaceutical compounds or inorganic compounds.

The inclusion of filter 402 allows for the collection of a fluid sample that is substantially free of fine particulate matter in sample collection vessels 106c and 106d. It is noted that using fluid sampling system 400 it is possible to collect samples which contain particulate matter (PM) in sample collection vessels 106a and 106b, and samples which are substantially free of particulate matter (PM), even fine particulate matter, in sample collection vessels 106c and 106d.

Referring next to FIGS. 8A-8C, shown therein is an alternate embodiment of a configuration 800 of sample collection vessels 106a and 106b, including detachable filter assemblies 806a and 806b, respectively. It is to understood that configuration 800 can be used in conjunction with various embodiments of the fluid sampling systems of the present disclosure, including, for example, embodiments 100 and 200. Detachable filter assemblies 806a and 806b have a diameter d equal to the inside diameter of sample collection vessels 106a and 106b and are disposed within sample collection vessels 106a and 106b, respectively, to form bottom sections 812a and 812b, and top sections 811a and 811 b within sample collection vessels 106a and 106b, respectively, such that bottom sections 812a and 812b, and top sections 811a and 811 b are separated by detachable filter assemblies 806a and 806b. Furthermore, detachable filter assemblies 806a and 806b are attached to the terminal end portions of fluid conduit portions 123c and 123d, respectively. Detachable filter assemblies 806a and 806b also include filters 807a and 807b.

Referring to FIG. 8C, shown therein is detachable filter 806b in a first state s1 and a second state s2. In first state s1, detachable filter 806b is attached to and secured in place to fluid conduit portion 123d, via support ring 808b which is a part of detachable filter 806b. Support ring 808b includes fastening screw 809b, penetrating the ring wall of supporting ring 808b. Upon loosening of fastening screw 809b fluid conduit portion 123d may be moved upwards (u) through support ring 808b, and in this manner, detachable filter assembly 806b may be removed from fluid conduit portion 123d, as shown in s2. It will be clear that similarly, detachable filter assembly 806b may be attached to fluid conduit portion 123d by inserting fluid conduit portion 123d into supporting ring 806b and fastening screw 809b to thereby secure filter assembly 806b in place.

Referring again to FIG. 8A, fluid flow (F) through filter assemblies 806a and 806b is such that fluid entering sample collection vessels 106a and 106b is filtered by filter 807a and 807b respectively, prior to fluid migrating from bottom sections 812a and 812b of sample collection vessels 106a and 106b to top sections 811a and 811 b of sample collection vessels 106a and 106b. Thus, filter assemblies 806a and 806b may be used to collect fluid constituents, notably insoluble particulates that are unable to traverse filters 807a and 807b, by retaining such particulates in sample vessels 106a and 106b, respectively, in suspension in bottom sections 812a or 812b. Furthermore, filter assemblies 806a and 806b may be used to collect fluid constituents which adhere to filter 807a and 807b. Upon removal of filter assemblies 806a and 806b, these fluid constituents may be evaluated by evaluation of filters 807a and/or 807b.

Filters 807a and 807b can, for example, be filters having a pore size of from about 0.25 μm to about 5 μm, for example, 0.5 μm, 1 μm, 1.5 μm, 2 μm, 2.5 μm, 3 μm, 3.5 μM, 4 μm, or 4.5 μm. The pore size may be selected based on the particulate containing fluid being collected. Filters 807a and 807b may be fabricated from different materials, including for example, polyethersulfone (PES) or polyvinylidene fluoride (PVDF). Filters 807*a* and 807*b* may further include specific sorbents as a receiving phase. Sorbent materials in this respect may include copolymer poly(divinybenzene)-co-N-vinylpyrrolidone, styrene/divinylbenzene (e.g., Dowex Optipore®), (poly)styrene-divinyl benzene, or a polymethacrylate, or surface modified forms thereof (e.g., Strata-X®, a surface modified N-vinylpyrrolidone), such as described in U.S. Pat. No. 7,119,145, which may be used to capture illicit drugs, pharmaceuticals, endocrine disrupting substances, personal care products, or (poly)phenol, for example. Furthermore, the filter may be assembled as a polar organic chemical integrative sampler (POCIS) (see: U.S. Pat. No. 6,478,961). As noted, upon completion of the sampling, filters 807*a* and 807*b* may be released (i.e., removed) and the fluid source material retained by filters 807*a* and 807*b* may be analyzed, for example, for the presence of chemical and biological entities therein, such as Illicit drugs, pesticides, microplastics, pharmaceuticals, bacteria, algae, viruses, pathogens, industrial contaminants, perfluoroalkyl and polyfluoroalkyl substances (PFAS), human biomarkers, or endocrine disrupting substances.

Next, another example embodiment of an openable container will be further discussed. Referring next to FIGS. 6A-6D shown therein is example openable container 102, which includes elements of fluid sampling system 300 shown in the schematic view shown in FIG. 4. It is to be understood that example openable container 102 generally can be used in conjunction with other fluid sampling systems in accordance with the present disclosure, including example fluid sampling systems 100, 200, and 400.

Thus, referring next to FIGS. 6A-6D openable container 102 includes lid 602 and hinges 604 to allow opening and closing of container 102. Lid 602 can be securely closed by clips or latches 606*a* and 606*b*. It is generally preferable to construct openable container 102 from a sturdy durable material, such as a more or less contiguous hard plastic, e.g., a polypropylene, a polystyrene, a polycarbonate, a polyamide, or the like, having a thickness of from about 0.25 cm to about 1 cm. Furthermore, it is noted that since openable container 102 may come into contact with fluid sources, openable container 102 is generally preferably constructed so that upon closure of openable container 102, the container 102 has a substantially watertight seal, and is impervious to entry of fluids into interior compartments 104, 108, 114 and 136 from exterior 130, other than via fluid inlet 118. Openable container 102 further includes hand grip 124 to allow for easy transport of openable container 102, for example, to a location in close proximity of a fluid sampling site, as well as linking portions 128*a* and 128*b* for attaching a suspension arrangement 126 thereto (as shown in FIG. 1). Openable container 102 further includes releasable attachment devices (not shown) to securely and releasably attach sample collection vessels 106*a*, 106*b*, 106*c* and 106*d* into compartment 104 (not shown). Examples of releasable attachment devices include clips, straps, or the like, to operably match the geometry of sample collection vessels 106*a*, 106*b*, 106*c* and 106*d*.

It is further noted that fluid outlet 120 and second portion 118*b* of fluid inlet 118 are similarly preferably constructed from a sturdy durable material. First portion 118*a* of fluid inlet 118, on the other hand, is preferably constructed from a more flexible material to form a flexible fluid line. First portion 118*a* may also have a significant length, for example, at least about 1 m, at least about 2 m, or at least about 7 m. This allows, for openable container 102 to be suspended in, for example, a manhole, in such a manner that openable container 102 is suspended above the fluid level, while portion 118*a* extends below the fluid level of fluid source 131. As shown in FIG. 6B, fluid inlet 118 and fluid outlet 120 can be rotatably attached to the exterior of side wall 605 of container 102 using a rotatable attachment. The rotatable attachment provides further flexibility and helps establish or maintain a fluidic coupling between fluid source 131 and fluid inlet 118. Furthermore, the rotational flexibility of fluid inlet 118 and fluid outlet 120 can prevent breakage of fluid inlet 118 or fluid outlet 120, for example, when fluid levels of fluid source 131 rapidly surge, and fluid inlet 118 and fluid outlet 120 become subject to upward fluid pressure.

It is further noted that in some embodiments, interior compartment 104, housing sample collection vessels 106*a*, 106*b*, 106*c* and 106*d*, may be cooled for example to a temperature in a range of from about 2° C. to about 10° C. Accordingly, compartment 104 may be referred to as a coolable compartment. Cooling of compartment 104 can be desirable to prevent alteration in the fluid constituents while the collected fluid samples await analysis. Cooling may be achieved, for example, by configuring the coolable compartment 104 to include releasable ice packs, e.g., a plastic container or bag filled with a refrigerant gel or liquid. In other embodiments, a thermoelectric cooling system may be included, for example, a cooling system based on Peltier plates. In such embodiments, in order to control the temperature in interior compartment 104, a thermostat may be installed in interior compartment 104. The thermostat may be operably coupled to controller 112, thus allowing an operator of the sampling system to control the temperature within compartment 104 by remotely monitoring the temperature of interior compartment 104. For example, the controller 112, in conjunction with a communication unit, may receive temperature measurements from the thermostat and transmit the temperature measurements to the operator who can then send a thermostat control signal to the controller 112 so that the controller 112 may alter the operation of the thermoelectric cooling system to maintain a desired temperature in the compartment 104. Alternatively, the controller 112 may be provided with software instructions for automatically controlling the thermoelectric cooling system by receiving temperature measurements from the thermostat, comparing the temperature measurements with a desired temperature range for the compartment 104 and if the temperature measurements are outside of the desired temperature range applying a control signal to adjust the thermostat until the measured temperature is within the desired temperature range described earlier. It is noted that in embodiments hereof, in which compartment 104 is cooled, it is preferable that interior wall 132*c* and the portion of the exterior wall 134 together forming interior compartment 104 are constructed to include insulation material to minimize temperature increases caused by heat transfer from the exterior, using, for example, an insulating foam or reflective insulation tape.

Methods for operating the sampling systems of the present disclosure will next be discussed. In general terms, in an aspect hereof, in an example embodiment, the present disclosure includes a method of collecting fluid samples comprising installing the sampling system of the present disclosure, while the container is in a closed position, in such a manner that the fluid inlet is fluidically coupled to a particulate containing fluid source. Following installation, the fluid pump, which is controlled by a controller is activated at a first time (e.g., an activation time) to cause a portion of the particulate containing fluid source to enter into the container through the fluid inlet and flow through the container through the fluid flow path. The pump is then deactivated at a second time (e.g., a deactivation time). Thereafter the sampling system is retrieved from the fluid source.

Figure 7A:
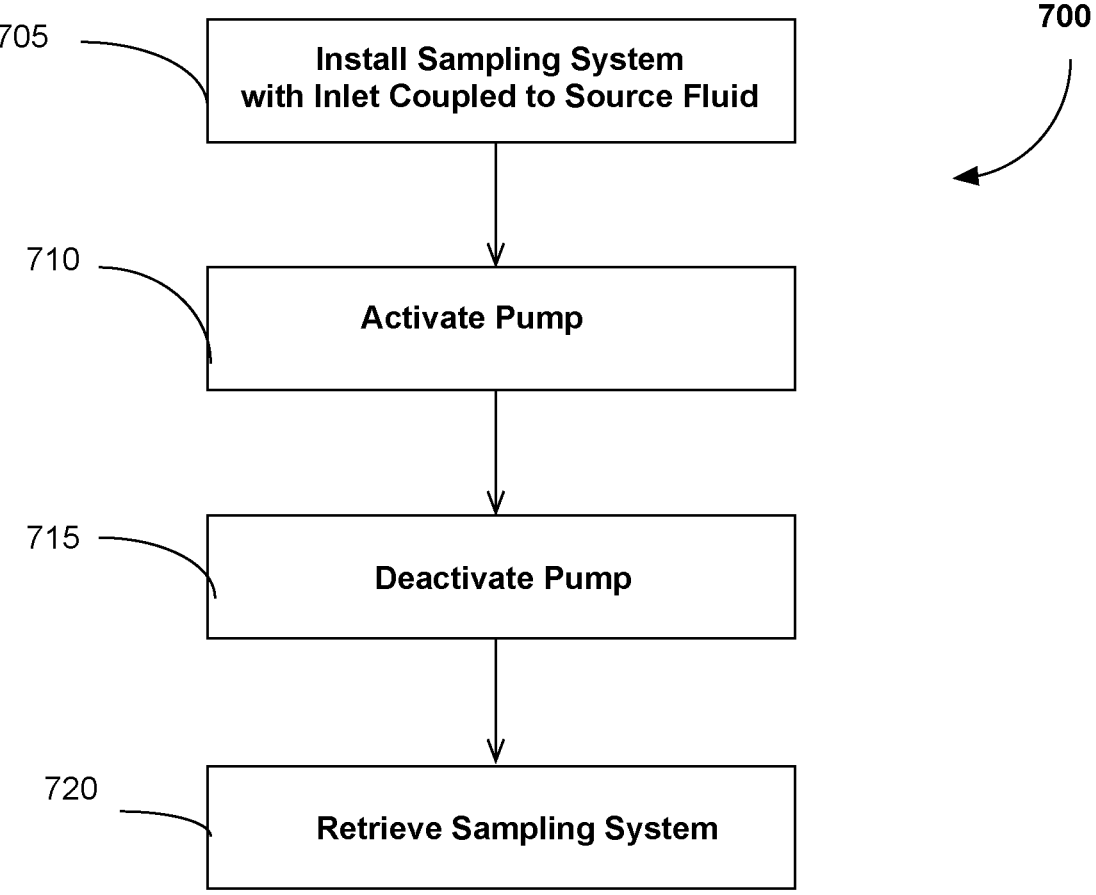
FIGS. 7A-7D are flow charts showing example embodiments of a method of collecting samples using the sampling system of FIG. 4.

Referring next to FIGS. 7A-70 shown therein are flowcharts showing example embodiments of methods 700, 701, 702 and 703, respectively, for collecting sample materials using one of the fluid sampling systems of the present disclosure in accordance with the teachings herein. Methods 700, 701, 702 and 703 refer to fluid sampling system 300 of FIG. 4 for illustrative purposes only and it should be understood that methods 700, 701, 702 and 703 can be applied to alternative embodiments of the fluid sampling systems, including fluid sampling systems 100, 200 and 400 shown in FIG. 1, FIG. 3, and FIG. 5, respectively.

Referring to FIG. 7A, at act 705 of method 700, the fluid sampling system is installed in a such a manner that fluid inlet 118, is fluidically coupled to fluid source 131. The fluid sampling system is installed while openable container 102 is in a closed position. In general, this involves installing the fluid sampling system 300 in such a manner that fluid inlet 118, notably at least the end portion of first portion 118a of fluid inlet 118 is submerged into fluid source 131. Furthermore, typically, and preferably, the fluid sampling system 300 is installed in such a manner that prolonged contact between the fluid source 131 and the openable container 102 is avoided to limit potential adverse effects caused by fluid source 131 of which the constituents may not be known, and which may include for example, harsh chemicals. However, provided that when openable container 102 is constructed such that when it is in a closed position it is impervious to fluid, occasional fluid contact, for example during installation, sampling or retrieval, is not generally expected to cause any adverse effects. In certain selected embodiments, installation of the fluid sampling system 300 may involve suspending the fluid sampling system above fluid source 131 in such a manner that first portion 118a of fluid inlet 118 can extend downwards into fluid source 131. It is noted that fluid source 131 can be any fluid source, notably any particulate containing fluid source, including any flowing fluid source or stagnant fluid source, and further including, without limitation, any flowing wastewater source or stagnant wastewater source or effluent source, including any domestic, municipal or industrial wastewater source, for example. Thus, in one example, the fluid sampling system 300 may be suspended downwards in a manhole leading to a sewer, for example, by connecting suspension arrangement 126 to a manhole grating of cover.

At act 710 of method 700, peristaltic fluid pump 110 is activated to initiate the flow of fluid through fluid path 122 through openable container 102 so that fluid can be received by sample collection vessels 106a, 106b, 106c and 106d. As previously noted, controller 112 may be used to activate peristaltic fluid pump 110 and initiate pumping of fluid from the fluid source 131 into openable container 102 at a specific time (e.g., a predefined activation time).

At act 715, once sample collection vessels 106a, 106b, 106c and 106d, have received sample fluid, peristaltic fluid pump 110 may be deactivated and fluid pumping may be stopped at a specific time. As previously noted, controller 112 may be used to deactivate the peristaltic fluid pump 110 at a specific time (e.g., a deactivation time) or the controller 112 may be used to monitor the amount of sample fluid within the fluid sampling system 300, determine when the sample collection vessels on vessels 106a, 106b, 106c and 106d, have been filled with sample fluid and then stop fluid pumping of peristaltic fluid pump 110.

At act 720, the fluid sampling system 300 may be retrieved from the sampling site. For example, when the fluid sampling system 300 is suspended in a manhole using suspension arrangement 126, the fluid sampling system 300 may be retrieved by pulling the fluid sampling system 300 upwards and out of the manhole using suspension arrangement 126.

Figure 7B:
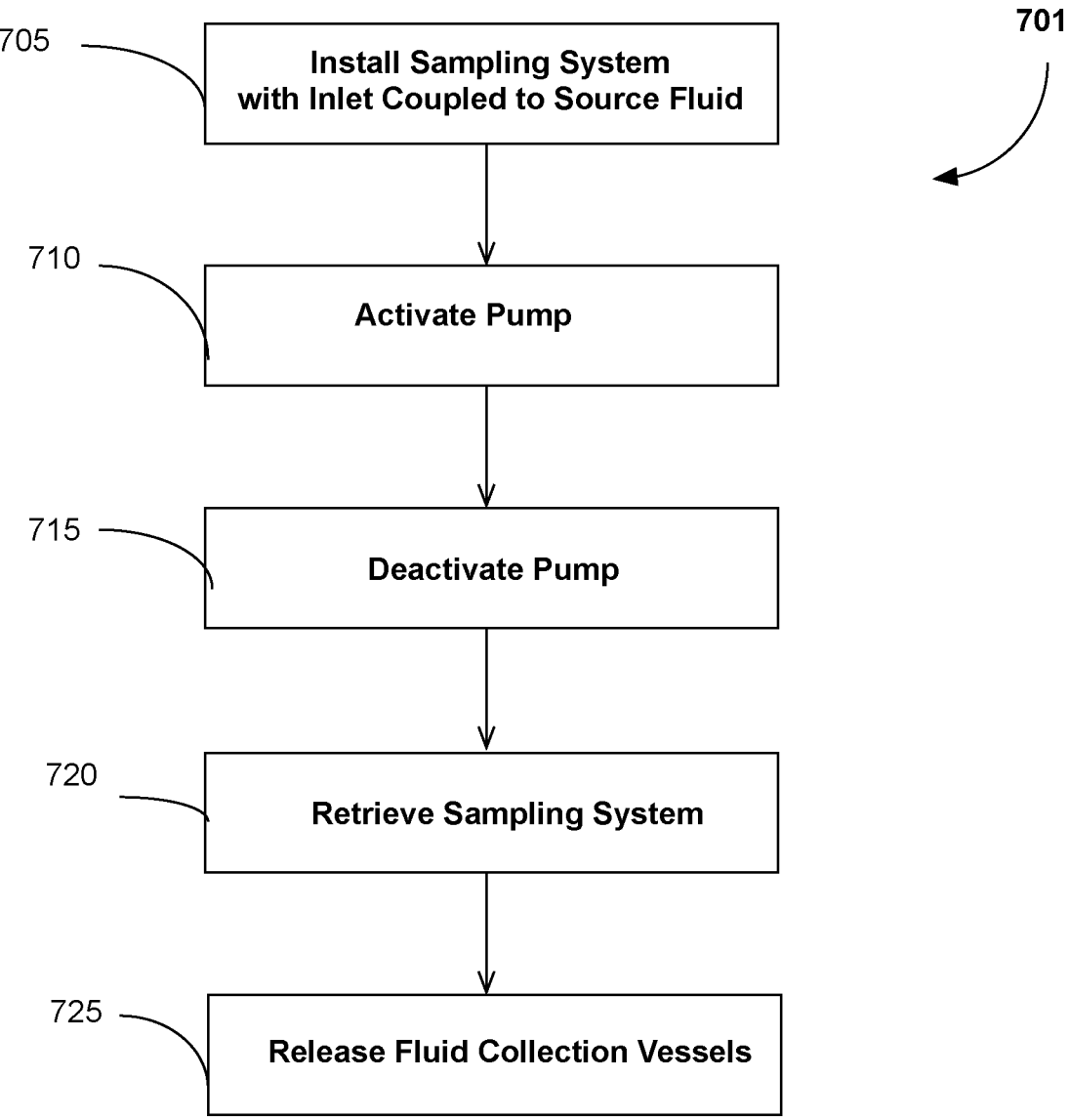

Referring next to FIG. 7B, it is noted that example method 701 includes acts 705, 710, 715 and 720, as previously described with respect to example method 700 and FIG. 7A. Method 701, additionally includes act 725. At act 725, sample collection vessels 106a, 106b, and optionally additional sample collection vessels are released from openable container 102. As previously noted, sample collection vessels 106a, 106b, 106c and 106d are releasably installed within compartment 134. Thus, upon opening openable container 102, sample collection vessels 106a, 106b, 106c and 106d can readily be released and separated from openable container 102.

Figure 7C:
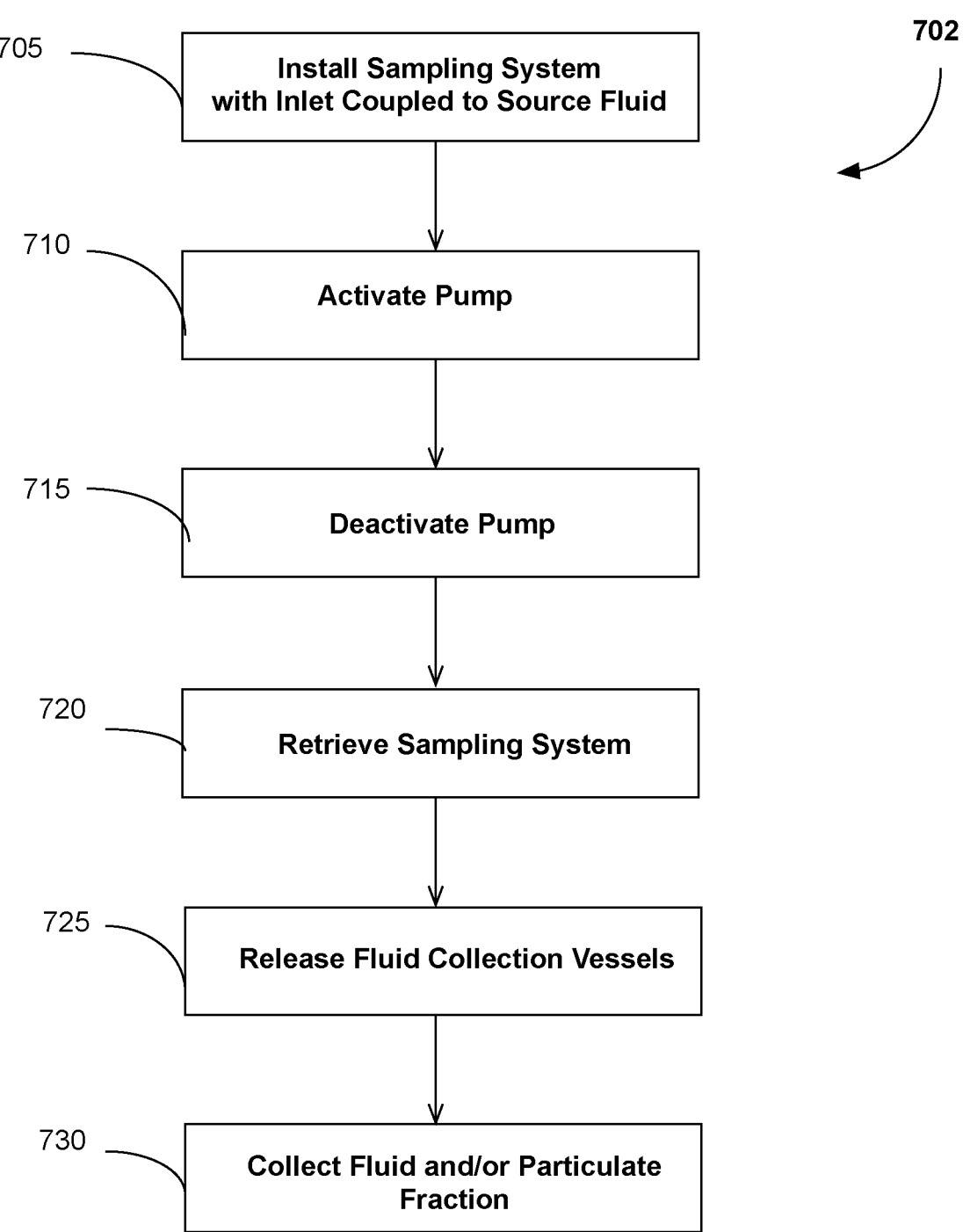

Referring next to FIG. 7C, it is noted that example method 702 includes acts 705, 710, 715 720 and 725, as previously described with respect to example methods 700 and 702 and FIGS. 7A and 7B, respectively. Method 702, additionally includes act 730. At act 730, fluid and/or particulate fractions are collected from collection vessels 106a, 106b, 106c and 106d. Such fraction collection may occur at a laboratory site following transport of the sample collection vessels thereto, whether contained in openable container 102, or separately following release from openable container 102. Fraction collection may occur at the sampling site, or, for example, at a laboratory.

Figure 7D:
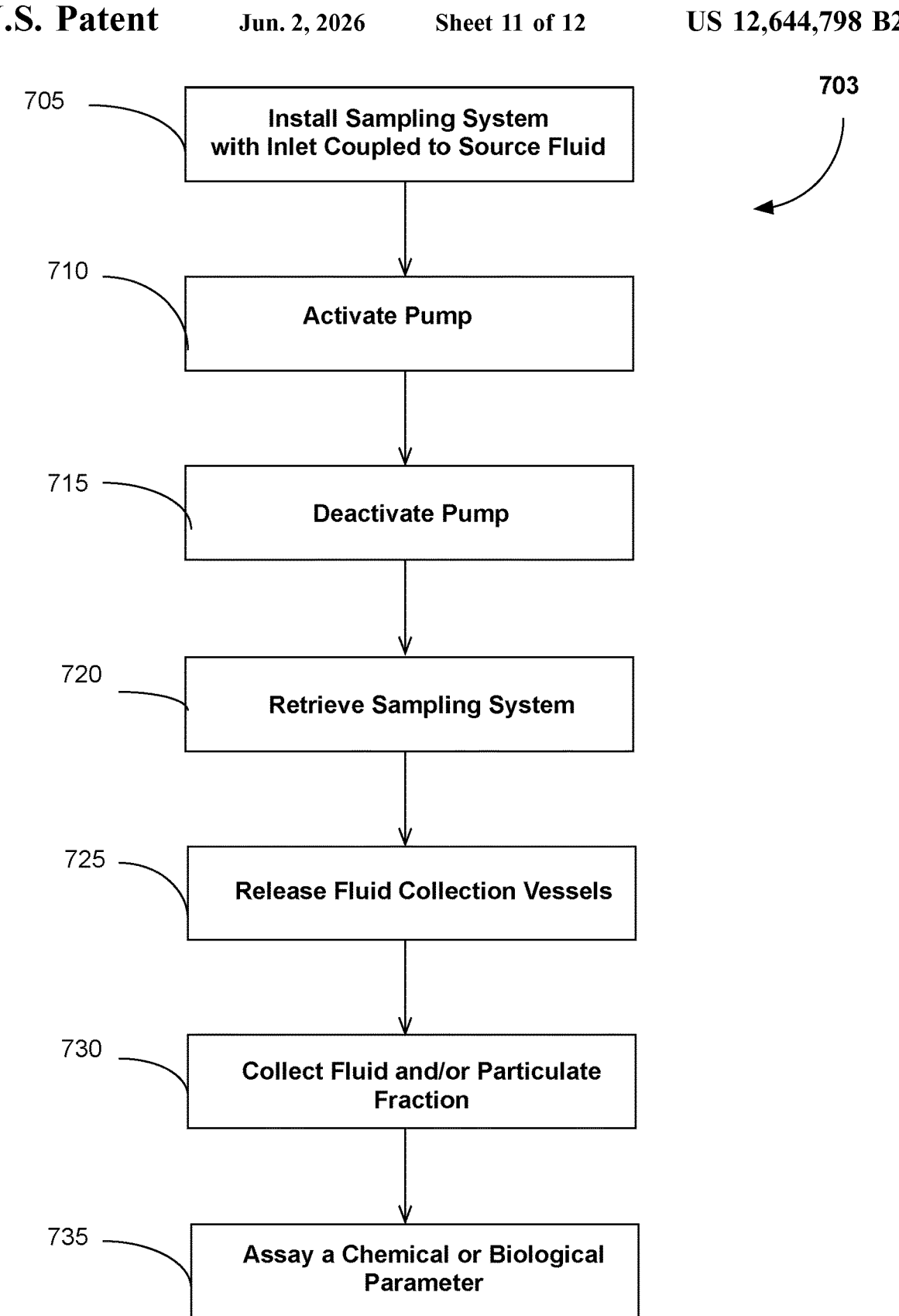

Referring next to FIG. 7D, it is noted that example method 703 includes acts 705, 710, 715 720, 725, and 730 as previously described with respect to example methods 700, 701 and 702 and FIGS. 7A, 7B, and 7C, respectively. Method 703, additionally includes act 735. At act 735, fluid and/or particulate fractions that are collected at act 730 are then assayed for a chemical or biological parameter. The exact chemical or biological parameter may vary and may be selected as desired. The assay may be performed at the fluid sampling site or following transport to a laboratory. Example parameters that may be assayed include, without limitation, chemical entities, including for example, heavy metals, such as cadmium (Cd), lead (Pb), chromium (Cr). Mercury (Hg) or nickel (Ni), and further including, without limitation, pharmaceutical compounds, illicit drug compounds, industrial pollutants or toxins, or agrochemical compounds. Biological compounds that may be assayed for are microbial pathogens, including, without limitation, bacterial pathogens, including, for example, enteric bacterial pathogens such as *Escherichia cob*, *Campylobacter* species, *Vibrio* species, *Salmonella* species, and Clostridioides species; viral pathogens, including, for example, corona viruses (e.g., SARS-CoV-2), Zika virus, adenovirus, hepatitis virus (A and E), Norwalk virus, and protozoal species, for example *Entamoebe* species and *Giardia* species. Furthermore, it will be understood by those of skill in the art that the assay that will be performed will vary depending on the selected chemical or biological parameter.

It will be clear from the foregoing that the fluid sampling systems of the present disclosure, upon having been deployed to collect sample materials, may be manipulated to collect sample collection vessels, which in turn may be used to collect particulate and/or liquid fractions. Accordingly, in a further aspect, the present disclosure provides, in at least one aspect, in at least one embodiment, a use of a fluid sampling system of the present disclosure to collect from each sample collection vessel a particulate fraction and/or a liquid fraction.

It will further be clear from the foregoing that collected particulate and/or liquid fractions may be assayed. Accordingly, in a further aspect, the present disclosure provides, in at least one aspect, a use of a settled particulate fraction and/or a liquid fraction collected using a sampling system of the present disclosure to assay a chemical or biological parameter therein.

As can now be appreciated, the fluid sampling systems of the present disclosure can be used for collecting sample materials from particulate containing fluid sources. The sample materials are collected in sample collection vessels contained in the container and can be used to assay for chemical or biological parameters.

Of course, the above described example embodiments of the present disclosure are intended to be illustrative only and in no way limiting. The described embodiments are susceptible to many modifications of composition, details and order of operation. Various embodiments of the invention, rather, is intended to encompass all such modifications within its scope, as defined by the claims, which should be given a broad interpretation consistent with the description as a whole.

The invention claimed is:

1. A sampling system for collecting particulates from fluid containing particulate matter, the sampling system comprising:
    an openable container comprising a lid configured to position the openable container in a closed position during operation periods of the sampling system;
    a fluid inlet configured to receive fluid containing particulate matter from outside the openable container and introduce the fluid containing particulate matter into the openable container;
    at least two serially fluidically coupled sample collection vessels releasably installed in the openable container and coupled to the fluid inlet, the at least two serially fluidically coupled sample collection vessels including a first sample collection vessel nearest the fluid inlet at a first distance from the fluid inlet and a final sample collection vessel distal to the fluid inlet at a second distance from the fluid inlet wherein the second distance is greater than the first distance;
    a fluid flow path extending from the fluid inlet, through the openable container and through the at least two serially fluidically coupled sample collection vessels;
    a fluid pump operably coupled to the fluid flow path and configured to induce flow of the fluid containing particulate matter through the fluid flow path; and
    a controller configured to control the flow of the fluid containing particulate matter through the fluid flow path by inducing the fluid containing particulate matter to enter the openable container through the fluid inlet, flow through the fluid flow path and sequentially flow through the at least two serially fluidically coupled sample collection vessels during an operation period of the sampling system wherein the openable container is in the closed position by (1) activating the fluid pump at a rate such that particulates in the fluid containing particulate matter settles in the at least two serially fluidically coupled sample collection vessels, and by (2) stopping collection of the fluid containing particulate matter by deactivating the fluid pump after the operation period.

2. The sampling system according to claim 1, further comprising a fluid outlet in fluid communication with the final sample collection vessel and with the outside of the openable container, wherein the fluid flow path further extends from the final sample collection vessel to the fluid outlet.

3. The sampling system according to claim 2, wherein the rate is selected such that a first quantity of the particulates settles in the first sample collection vessel and a second quantity of the particulates settles in the final sample collection vessel wherein the first quantity is greater than the second quantity.

4. The sampling system according to claim 1, wherein the at least two serially coupled sample collection vessels includes at least three serially fluidically coupled sample collection vessels.

5. The sampling system according to claim 1, wherein the fluid flow path comprises a fluid coupling system for at least one of the at least two serially fluidically coupled sample collection vessels having a height, the fluid coupling system comprising a sample collection vessel fluid inlet and a sample collection vessel fluid outlet disposed in the at least one of the at least two serially fluidically coupled sample collection vessels, the sample collection vessel fluid inlet comprising a tubular fluid inlet conduit traversing a top portion of the at least one of the at least two serially fluidically coupled sample collection vessels at a first aperture and extending downwards from the first aperture to a bottom portion of the at least one of the at least two serially fluidically coupled sample collection vessel such that fluid incoming from the bottom of the at least one of the at least two serially fluidically sample collection flows into the first aperture, and the sample collection vessel fluid outlet comprises a tubular fluid outlet conduit traversing the top portion of the at least one of the at least two serially fluidically coupled sample collection vessels at a second aperture and extending downwards the second aperture and no further than to approximately half the height of the at least one of the at least two serially fluidically coupled sample collection vessels such that fluid outgoing from the at least one of the at least two serially fluidically coupled sample collection vessels transfers downstream the at least one of the at least two serially fluidically coupled sample collection vessels.

6. The sampling system according to claim 1, wherein the fluid flow path includes a filter configured to collect selected chemical or biological species from the fluid containing particulate matter, wherein the filter is either installed in the fluid flow path between the fluid inlet and the first sample collection vessel, or is installed in the fluid flow path between the first sample collection vessel and the final sample collection vessel.

7. The sampling system according to claim 5 wherein the filter is installed in the fluid flow path within the first sample collection vessel at a height above the height of a terminal end of the tubular fluid inlet conduit of the sample collection vessel fluid inlet such that incoming fluid flows into the at least one of the at least two serially fluidically coupled sample collection vessels and traverses the filter, and such that outgoing fluid after traversing the filter transfers downstream from the at least one of the at least two serially fluidically coupled sample collection vessels.

8. The sampling system according to claim 1, wherein the fluid inlet includes a terminal end extending to the outside of the openable container, and the terminal end includes a mesh filter configured to prevent entry of debris into the openable container.

9. The sampling system according to claim 1, wherein the openable container is compartmentalized and includes a coolable compartment configured to house the at least two serially fluidically coupled sample collection vessels.

10. The sampling system according to claim 9, wherein the coolable compartment is configured to hold ice packs.

11. The sampling system according to claim 9, wherein the openable container further includes a cooling device configured to control a set temperature of the coolable compartment in conjunction with a thermal controller.

12. The sampling system according to claim 11, wherein the set temperature is between about 2° C. and about 10° C.

13. The sampling system according to claim 1, wherein the controller is coupled to an environmental sensor capable of detecting a change in an environmental parameter, and is configured to activate the fluid pump upon receiving from the environmental sensor the detected change in the environmental parameter.

14. The sampling system according to claim 13, wherein the environmental sensor is selected from the group consisting of a rain sensor, a pH sensor, a temperature sensor, a turbidity sensor, a biochemical oxygen demand (BOD) sensor, a chemical oxygen demand (COD), an electrical conductivity (EC) sensor, and a total dissolved solids (TDS) sensor.

15. The sampling system according to claim 1, wherein the openable container comprises a linking portion configured to attach the openable container to a suspension arrangement.

16. The sampling system according to claim 7, wherein the filter is detachably installed in the fluid flow path within the first sample collection vessel.

17. A method of collecting samples using the fluid sampling system according to claim 1, the method comprising:

positioning the openable container in a closed position such that the fluid inlet is fluidically coupled to a source of fluid containing particulate matter;

introducing the fluid containing particulate matter into the openable container through the fluid inlet and inducing flow of the introduced fluid containing particulate matter through the fluid flow path by activating the fluid pump at a rate whereby particulates in the introduced fluid containing particulate matter separate from the introduced fluid containing particulate matter and settle in the at least two serially fluidically coupled sample collection vessels;

deactivating the fluid pump;

with the fluid pump deactivated, detaching the at least two serially fluidically coupled sample collection vessels from the openable container; and retrieving the openable container.

18. The method according to claim 17, further comprising activating and deactivating the fluid pump an additional or more times before detaching the at least two serially fluidically coupled sample collection vessels from operable container.

19. The method according to claim 18, wherein the activating the fluid pump and the deactivating the fluid pump the additional or more times, is separated by a hold time interval of at least 15 minutes during which no fluid flows through the fluid path and the operation period is between about 5 seconds and about 30 seconds.

20. The method according to claim 17, wherein the fluid containing particulate matter is wastewater.

* * * * *